US008147562B2

(12) United States Patent
Vacanti et al.

(10) Patent No.: US 8,147,562 B2
(45) Date of Patent: Apr. 3, 2012

(54) THREE DIMENSIONAL CONSTRUCT FOR THE DESIGN AND FABRICATION OF PHYSIOLOGICAL FLUIDIC NETWORKS

(75) Inventors: Joseph P. Vacanti, Winchester, MA (US); Jeffrey Borenstein, Holliston, MA (US); Mohammad R. Kaazempur-Mofrad, Lafayette, CA (US); Eli Weinberg, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 549 days.

(21) Appl. No.: 10/528,737

(22) PCT Filed: Sep. 23, 2003

(86) PCT No.: PCT/US03/29880
§ 371 (c)(1),
(2), (4) Date: Oct. 26, 2005

(87) PCT Pub. No.: WO2004/026115
PCT Pub. Date: Apr. 1, 2004

(65) Prior Publication Data
US 2006/0136182 A1 Jun. 22, 2006

Related U.S. Application Data

(60) Provisional application No. 60/412,981, filed on Sep. 23, 2002, provisional application No. 60/449,291, filed on Feb. 21, 2003.

(51) Int. Cl.
*A61F 2/02* (2006.01)
(52) U.S. Cl. ............ 623/23.72; 623/1.1; 623/1.44; 435/325; 435/395; 435/401; 422/502; 137/803; 137/814
(58) Field of Classification Search .......... 435/325, 435/347, 395, 397, 401; 422/68.1, 99; 73/861, 73/861.71
See application file for complete search history.

(56) References Cited

U.S. PATENT DOCUMENTS

| | | |
|---|---|---|
| 3,684,097 A | 8/1972 | Mathewson, Jr. et al. |
| 3,839,204 A | 10/1974 | Ingenito et al. |
| 3,892,533 A | 7/1975 | Freedman et al. |
| 3,927,981 A | 12/1975 | Viannay et al. |
| 3,977,976 A | 8/1976 | Spaan et al. |
| 4,008,047 A | 2/1977 | Petersen |
| 4,176,069 A | 11/1979 | Metz et al. |
| 4,191,182 A | 3/1980 | Moncrief et al. |
| 4,229,290 A | 10/1980 | Raj |
| 4,666,668 A | 5/1987 | Lidorenko et al. |
| 5,034,188 A | 7/1991 | Nakanishi et al. |
| 5,110,548 A | 5/1992 | Montevecchi et al. |
| 5,222,982 A | 6/1993 | Ommaya |
| 5,225,161 A | 7/1993 | Mathewson et al. |
| 5,263,924 A | 11/1993 | Mathewson |
| 5,308,356 A | 5/1994 | Blackshear, Jr. et al. |
| 5,316,724 A | 5/1994 | Mathewson et al. |
| 5,601,727 A | 2/1997 | Bormann et al. |
| 5,626,759 A | 5/1997 | Krantz et al. |
| 5,695,717 A | 12/1997 | Polaschegg et al. |
| 6,022,743 A * | 2/2000 | Naughton et al. ............ 435/395 |
| 7,048,856 B2 | 5/2006 | Fissell, IV et al. |
| 7,191,110 B1 * | 3/2007 | Charbel et al. .................. 703/11 |
| 2002/0106311 A1 * | 8/2002 | Golbig et al. ................. 422/130 |
| 2002/0182241 A1 | 12/2002 | Borenstein et al. |
| 2003/0075498 A1 | 4/2003 | Watkins et al. |
| 2003/0129736 A1 | 7/2003 | Mitrani |
| 2004/0057869 A1 | 3/2004 | Dingley |
| 2006/0018838 A1 | 1/2006 | George et al. |
| 2007/0128171 A1 | 6/2007 | Tranquillo et al. |

FOREIGN PATENT DOCUMENTS

| | | |
|---|---|---|
| DE | 10000823 A1 | 7/2001 |
| JP | 60-181654 A | 9/1985 |
| JP | 6237992 A | 8/1994 |
| WO | 0038758 A1 | 7/2000 |
| WO | 02076529 A1 | 10/2002 |

OTHER PUBLICATIONS

Kane, R.S. et al. Patterning proteins and cells using soft lithography. Biomaterials. 1999. 20: 2363-2376.*
Borenstein, et al: "Microfabrication technology for vascularized tissue engineering", Biomedical Microdevices Kluwer Academic Publishers, USA, vol. 4, No. 3, Jul. 2002, pp. 167-175.
Cross "Fractals in Pathology." Journal of Pathology 182: 1-8 (1997).
Anderson et al. "Fabrication of Topologically Complex Three-Dimensional Microfluidic Systems in PDMS by Rapid Prototyping." Anal. Chem 72: 3158-3164 (2000).
Hediger et al. "Biosystem for the Culture and Characterisation of Epithelial Cell Tissues." Sensors and Actuators B 63: 63-73 (2000).
Borenstein et al. "Living Three-Dimensional Microfabricated Constructs for the Replacement of Vital Organ Function." Transducers 4C1.3: 1754-1757 (2003).
Stone "Microfluidics: Basic Issues, Applications, and Challenges." American Institute of Chemical Engineers Journal 47(6): 1250-1254 (2001).
Fairley "Blood from a Chip." Technology Review, p. 28 (2000).
Lim, et al., Lab Chip (2003), 3: 318-323.
Iwasaki et al, Science Direct (Aug. 2002), 23/16: 3421-3427.
Biomedical Materials; Polyimide membrane for use as artificial lung material, www.highbeam.com/doc/1G1-45103565. html, (Nov. 1, 1994).

* cited by examiner

*Primary Examiner* — Allison Ford
*Assistant Examiner* — Susan E Fernandez
(74) *Attorney, Agent, or Firm* — Edwards Wildman Palmer LLP; Peter C. Lauro, Esq.; George N. Chaclas, Esq.

(57) ABSTRACT

The present invention relates to methods for the design and fabrication of biological constructs, such as organ simulants or organ replacements, which contain complex microfluidic architecture. Designs of the present invention provide increased space in the lateral dimension, enabling a large number of small channels for small vessels.

19 Claims, 26 Drawing Sheets

A) Figure 12 B)

A)
E)
B)
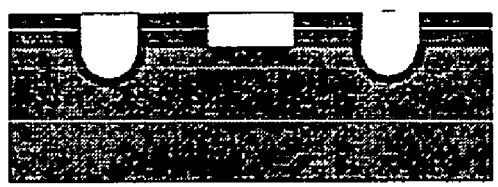
F)
C)
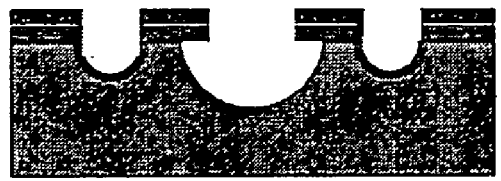
G)
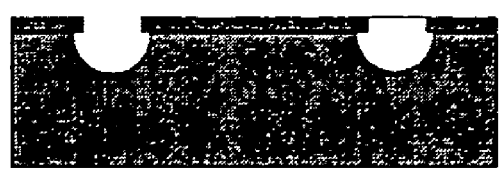
D)
H)
Figure 22

THREE DIMENSIONAL CONSTRUCT FOR THE DESIGN AND FABRICATION OF PHYSIOLOGICAL FLUIDIC NETWORKS

RELATED APPLICATIONS

This application is filed under 35 U.S.C. §371 as the U.S. national phase application of International Application PCT/US03/029880, having an international filing date of Sep. 23, 2003 and designating the U.S. and claiming priority from U.S. application Ser. No. 60/412,981, filed on Sep. 23, 2002, and U.S. application Ser. No. 60/449,291, filed on Feb. 21, 2003, the contents of which are incorporated herein by reference.

Reference is made herein to U.S. Ser. No. 10/187,247, a CIP of U.S. Ser. No. 10/187,247, filed Jun. 28, 2002, which claims priority to U.S. Ser. No. 60/367,675, filed Mar. 25, 2002, and which is a CIP of Ser. No. 09/560,480, filed Apr. 28, 2000, which claims priority to U.S. Ser. No. 60/165,329, filed Nov. 12, 1999 and to U.S. Ser. No. 60/131,930, filed Apr. 30, 1999, the contents each of which are expressly incorporated herein by reference.

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein can be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

STATEMENT OF POTENTIAL GOVERNMENT INTEREST

The United States government may have certain rights in this invention by virtue of grant number DAMD-99-2-9001 from The Center for Integration of Medicine & Innovative Technology.

FIELD OF THE INVENTION

The present invention generally relates to the fields of organ transplantation and reconstructive surgery, and to the field of tissue engineering. It more specifically provides methods for the design and fabrication of biological constructs, such as organ simulants or organ replacements, which contain complex microfluidic architecture. Such constructs can have high cell densities and physiologically realistic distributions of features such as capillaries, larger blood vessels and liver sinusoids, enabling them to support cells outside of the fluidic networks, just as true organs supply nutrients and oxygen and process waste in surrounding tissues.

BACKGROUND

Current methods of designing and producing organ simulants, organ assist devices or organ replacements include the use of transplanted organs from donor humans, transplanted organs from animals (i.e., xenografts), bioartificial mechanical devices and tissue-engineered organs.

Tissue-engineered organs have historically been attempted through the use of cell-seeded constructs. Initially, tissue engineered constructs were built using solid freeform fabrication technology, however, elements on the size scale of capillaries could not be built. Subsequent approaches to designing and building tissue engineered constructs entailed a microfabrication approach, which enabled the generation of two-dimensional microfluidic networks capable of simulating many features of human physiology, including the distribution of parameters such as vessel sizes, lengths and densities. Importantly, the microfabrication approach enabled capillary-sized features to be built. In the case of blood vessels, distribution of these parameters regulates important components of vascular function, including blood pressure, blood cell velocity, wall shear stress, hematocrit distribution, and the maximum distance between capillaries (which is limited by the diffusivity of oxygen in the tissue).

Once the two-dimensional microfluidic networks were designed, polymer scaffolds based on replica molding technology were constructed, and integrated into a three-dimensional architecture by folding, stacking or rolling the two dimensional sheets into a three dimensional configuration with large vertical inlet and outlet tubes linking the two dimensional networks. However, with this method, distribution of vessel network sizes is limited in three-dimensional integration. Branching networks are not truly three-dimensional, and vessels larger than the capillaries take up a large amount of available space within the two dimensional networks. This restraint imposes a limitation on the available space for small blood vessels, and as a result, the tissue engineered constructs suffer from non-physiological pressures and fluid velocities. If a larger number of the mid-sized vessels could be arranged vertically, more room in the two-dimensional networks could be made available for capillaries.

In true physiological blood vessel networks, 85% of the total cross-section of vessels lies in the smallest vessels, the capillaries (Guyton and Hall, *Textbook of Medical Physiology*, 10$^{th}$ Ed., W. B. Saunders (2000)). The human body utilizes the three-dimensional fractal branching nature of the vasculature to incorporate a large number of small vessels (Kaazempur-Mofrad et al., *Annals of Biomedical Engineering*, 29,154 (2001). This weighting of vessel distribution is necessary because the capillaries are performing the most crucial functions of the vasculature, namely, oxygen, nutrient and waste transport. All larger vessels are simply channels for the distribution of blood to and from the organs. According to morphometric models of the vascular system, vessels are organized into categories, or families, of sizes and this categorization allows for the characterization of a mathematical distribution of vessels upon which models for the networks may be developed (Bassingthwaighte et al., *Fractal Physiology* (Oxford, Oxford University Press, 1994); Kassab and Fung, *Am J Physiol* 267, H319 (1994); Pries et al., *Am J Physiol* 272, H2716 (1997); Fenton et al., *Microvasc Res* 29, 103 (1985); Pries et al., *Am J Physiol* 263, H1770 (1992); Kiani et al., *Am J Physiol* 266, H1822 (1994); Lipowsky et al.,

*Microvasc Res* 19, 297 (1980); Fung, *Biodynamics: Circulation*. (New York, Springer, 1984)). Improved three-dimensional models and designs that provide higher cell densities and a larger relative number of small vessels would contribute to enhanced methods and devices for tissue engineering.

OBJECTS AND SUMMARY OF THE INVENTION

Methods, compositions and devices of the present invention comprise novel designs for integration of two-dimensional constructs into three dimensions.

In one embodiment, the present invention comprises a composition comprising a physiological fluidic network having stacked, two-dimensional layers comprised of blood vessels, wherein small and/or midsized vessels in one layer are vertically connected to small and/or midsized vessels in at least one additional layer by vertical links.

In another embodiment, the present invention comprises a method of forming a fluidic network comprising the steps of stacking two dimensional layers comprised of small and/or midsized vessels and connecting said vessels within one layer to at least one additional layer with vertical links.

Current techniques utilize a single vertical link between two dimensional networks at the largest vessel diameter for the inlet and outlet, resulting in alternating horizontal sheets of vessels and unpatterned polymer stacked in the vertical dimension. The present invention provides complex methods of integrating the two dimensional networks, in which small and midsized vessels are arranged to link the networks vertically in a more complex manner. Methods, compositions and devices of the present invention enable higher cell densities and a larger relative number of small vessels to be incorporated into the three dimensional structure of tissue engineered constructs.

In one embodiment, designs of the present invention comprise stacked, folded or rolled series of two-dimensional layers, with the two-dimensional layers arranged such that large numbers of interconnection points exists between layers. Each two-dimensional layer is generated by using a computational fluid dynamic (CFD) model, which produces a model network to simulate the critical structure and function of the tissue or organ of interest. The CFD model generates multiple, preferably at least two, distinct two-dimensional layers, which are arranged to allow for a very large number of vertical interconnects between layers. Within each two-dimensional layer, unit cells are arranged in a hexagonal pattern, and the thickness of each line in the pattern corresponds to the width of the fluidic channel.

The resulting three-dimensional structure is comprised of a large number of two-dimensional layers, arranged in a repeating fashion, and are stacked vertically in a total stack of at least 15 layers. The present invention can comprise between about 50 and 2000 layers, more preferably between about 100 and 1000 layers and most preferably about 500 layers. Advantageously, designs of the present invention have increased space in the lateral dimension, enabling a much larger number of small channels. It enables at least one order of magnitude but not more than two orders of magnitude increase in the number of small channels.

Preferably, methods, compositions and devices of the present invention provide tissue engineered constructs having a small vessel or capillary capacity in an amount greater than about 2000 capillaries/cc, greater than about 5000 capillaries/cc, greater than about 10,000 capillaries/cc, greater than about 15,000 capillaries/cc, up to about 100,000 capillaries/cc. Most preferably, methods of the present invention provide tissue engineered constructs having a small vessel or capillary capacity in an amount equal to or greater than about 10,000 capillaries/cc.

Tissue engineered constructs of the present invention maintain physiological pressure and fluid velocities in the network, maximum oxygen diffusion length, and vessel size distribution, which for small vessels is between about 100-200 microns. Blood vessels of all sizes are oriented along all three axes and along all angles in between. Simultaneous matching of all physiological parameters results from organization of tissues in a true three-dimensional coordinated fashion.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

In FIG. 11A, the pattern begins by branching in three directions from a single node. In FIG. 11B, the same branching pattern is applied to nodes other than the starting node. FIG. 11C shows the hexagonal pattern created by the fractal. FIG. 11D shows that the pattern can be allowed to grow to any size.

FIG. 12A shows layer B; FIG. 12B shows layer D.

FIG. 13A shows layer A; FIG. 13B shows layer C; FIG. 13C shows layer E; and FIG. 13D shows layer F.

FIG. 20 shows a full network appropriate for use as support for a tissue engineered organ.

FIG. 22 shows a more detailed schematic describing a process for the production of a complex structure comprising channels wherein all channels do not have the same depth. The steps of the process are as follows: The process begins with a substrate wafer (A); Masking material is deposited (B); Masking material is patterned (C); Substrate wafer is etched (D); a second masking layer is deposited (E); The second masking layer is patterned (F); The substrate wafer is etched again (G); The masking layer is removed (H).

DETAILED DESCRIPTION

Figure 1A:
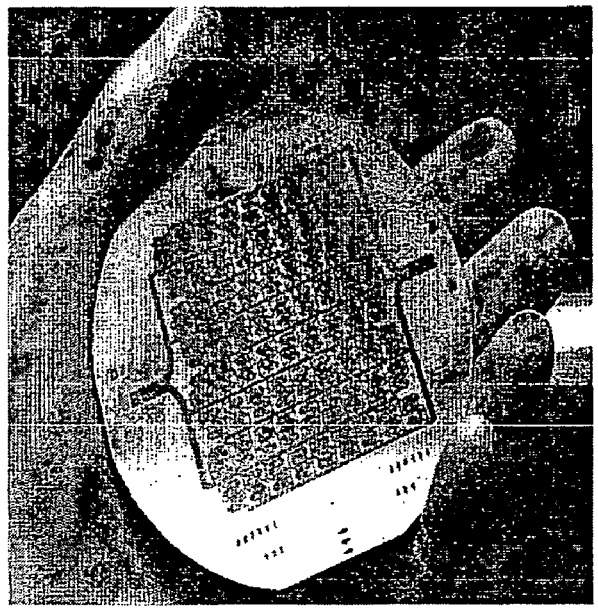
FIG. 1A shows a silicon wafer with a network of microchannels.

The invention provides methods for the design and fabrication of biological constructs, such as organ simulants or organ replacements, which contain complex microfluidic architecture. The methods, compositions and devices of the invention employ a new approach for fabricating three-dimensional vascularized tissues for transplantation in human recipients in need of vital organs and other tissues requiring a blood supply.

Advantages of this invention over other methods of tissue engineering include high cell densities and physiologically realistic distributions of features such as capillaries, other larger vessels and liver sinusoids, enabling support of cells outside of the fluidic networks, just as true organs supply nutrients and oxygen and process waste in surrounding tissues.

In one embodiment, the present invention comprises a composition comprising a physiological fluidic network having stacked, two-dimensional layers comprised of blood vessels, wherein small and/or midsized vessels in one layer are vertically connected to small and/or midsized vessels in at least one additional layer by vertical links.

In another embodiment, the present invention comprises a method of forming a fluidic network comprising the steps of stacking two dimensional layers comprised of small and/or midsized vessels and connecting said vessels within one layer to at least one additional layer with vertical links.

Preferably, methods, compositions and devices of the present invention provide tissue engineered constructs having a small vessel or capillary capacity in an amount greater than about 2000 capillaries/cc, greater than about 5000 capillaries/cc, greater than about 10,000 capillaries/cc, greater than about 15,000 capillaries/cc, up to about 100,000 capillaries/cc. Most preferably, methods of the present invention provide tissue engineered constructs having a small vessel or capillary capacity in an amount equal to or greater than about 10,000 capillaries/cc.

In a preferred embodiment, the present invention comprises a tissue engineered construct, wherein the small blood vessel capacity is at least about 10,000 capillaries/cc and the distance between small blood vessels is less than about 200 microns.

Methods, compositions and devices of the present invention can further comprise cells including, but not limited to, smooth or skeletal muscle cells, myocytes, fibroblasts, chondrocytes, adipocytes, fibromyoblasts, ectodermal cells, hepatocytes, kidney cells, pancreatic islet cells, intestinal cells osteoblasts, hematopoietic cells and stem cells.

As used herein, the term "vessel" and blood vessel" are interchangeable.

A "small vessel" or "capillary" refers to a blood vessel that is less than 20 microns in diameter.

A "midsized vessel" refers to a blood vessel that is between 20 and 100 microns in diameter.

"Physiological" refers to the condition of a blood vessel within a normal living system. In context, "physiological" can also refer to the condition of a tissue or organ within a normal living system. A "condition" refers to one or more parameters, such as pressure, velocity and capacity of blood flow, shear wall stress, hematocrit distribution and distance between vessels, which for small vessels is between about 100-200 microns. Data from two physiological systems are described in Kassab et al, Am J Physiol 265 (1): H350 (1993) and Kassab, Ann Biomed Eng 28 (8): 903 (2-000) the contents of which are incorporated herein by reference.

A "vertical link" refers to a partial or complete through hole within one layer that vertically connects at least one second layer. Vertical links are perpendicular to the layers which they connect. An "inlet" or "outlet" refers to the placement of tubing within a through hole.

Thus, the invention provides scalable techniques for producing organs, or portions thereof, large enough to transplant into a subject, such as animal recipients, typically vertebrate recipients, and preferably human recipients. A "subject" is a vertebrate, preferably a mammal, and most preferably a human. Mammals include, but are not limited to, humans, farm animals, sport animals, and pets. One of skill in the art can readily vary the parameters of the methods described herein to accommodate hosts or subjects of variable size and species, including but not limited to, humans of any age.

As used herein, the terms "comprises", "comprising", and the like can have the meaning ascribed to them in U.S. Patent Law and can mean "includes", "including" and the like.

Manufacture of Molds and Polymer Scaffolds

For purposes of this invention a "mold" is a device on the surface of which the branching structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal.

Molds of the present invention can comprise a variety of materials, including, but not limited to, inert materials such as silicon, polymers such as polyethylene vinyl acetate, polycarbonate, and polypropylene, and materials such as a ceramic or material such as hydroxyapatite. In particular, the mold can comprise from metals, ceramics, semiconductors, organics, polymers, and composites. These materials are either inherently suitable for the attachment and culture of animal cells or can be made suitable by coating with materials described herein to enhance cell attachment and culture (e.g. gelatin, matrigel, vitrogen and other tissue culture coatings known in the art).

Figure 1B:
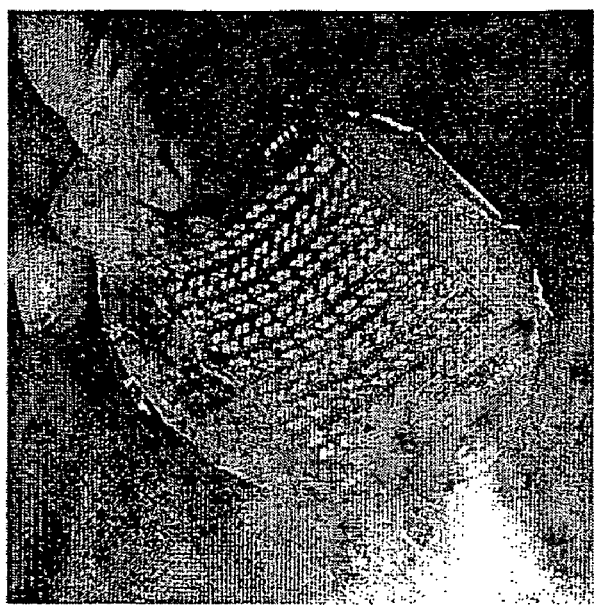
FIG. 1B shows a polymer scaffold with a network of microchannels.
Figure 2:
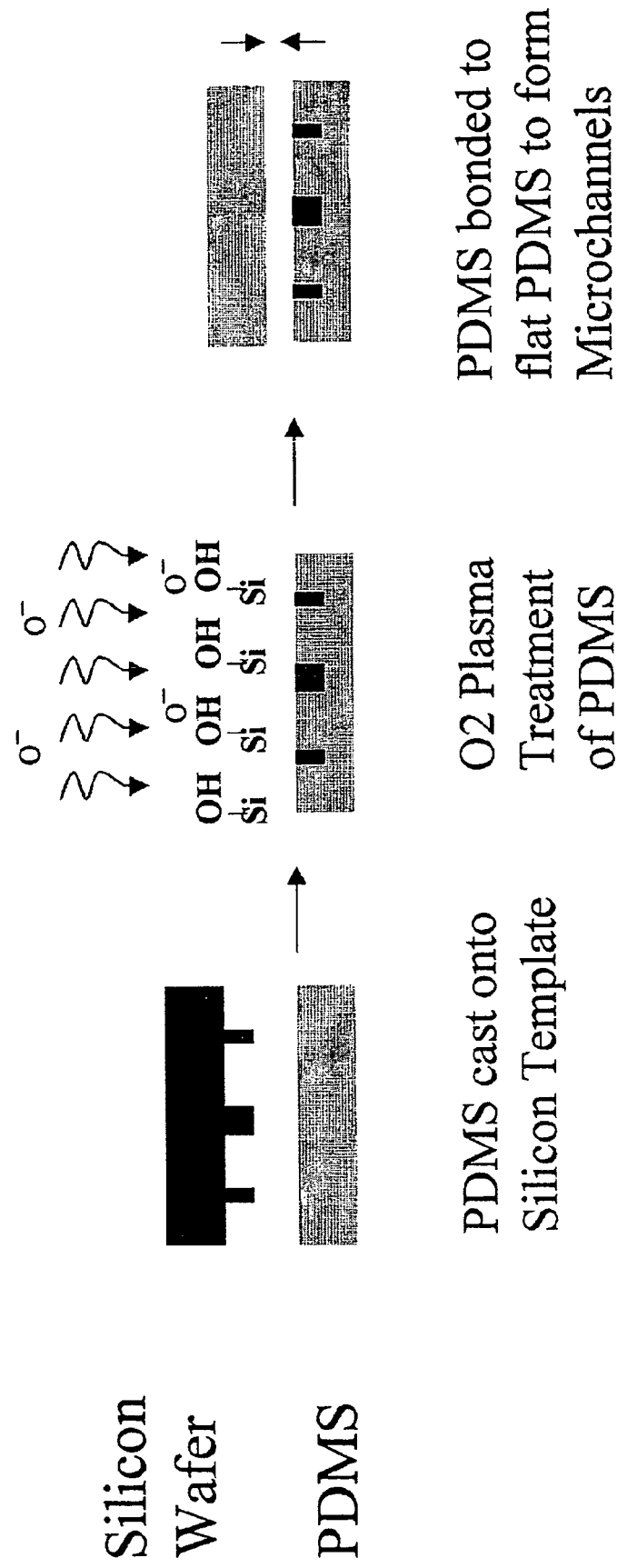
FIG. 2 shows a schematic diagram of one method for making a polymer scaffold from a micromachined silicon wafer using MEMS replica molding.

In an alternative embodiment, MEMS replica molding can be used to make a "polymer scaffold" for seeding cells. In this method, a mold is made as described herein, preferably of silicon (FIG. 1A), and is then used as a template on which a polymeric material is cast (FIG. 2). Optionally, the polymer scaffold can then be peeled away from the mold (FIG. 1B) and seeded with cells.

A "tissue-defining surface" is the surface of a mold or a polymer scaffold, and a "substrate" is the mold or polymer scaffold itself.

The term "polymer" includes polymers and monomers that can be polymerized or adhered to form an integral unit. The polymer can be non-biodegradable or biodegradable, typically via hydrolysis or enzymatic cleavage. For implantation, polymer scaffolds are preferably used, which can be biodegradable polymer scaffolds. For embodiments relating to extracorporeal support devices, biocompatible, nondegradable polymers may facilitate size reduction.

In one embodiment, the biodegradable polymer scaffold comprises biodegradable elastomers formed from hydrolyzable monomers as described in Wang et al, Nature Biotech 20, 602 (2002), the contents of which are incorporated herein by reference. These biodegradable elastomers are analogous to vulcanized rubber in that crosslinks in a three dimensional network of random coils are formed. These biodegradable elsatomers are hydrolyzed over time, preferably within 60 days.

Polymer material for implantation should be selected for biocompatibility. Any degradation products should also be biocompatible. Relatively high rigidity is advantageous so that the polymer scaffold can withstand the contractile forces exerted by cells growing within the mold. A biocompatible degradable polymer and its degradation products are non-toxic toward the recipient.

The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete loss of mass. The term "degrade" as used herein includes "completely degrade" unless otherwise indicated.

Materials suitable for polymer scaffold fabrication include, but are not limited to, poly-dimethyl-siloxane (PDMS), polyglycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, teflon RTM, nylon silicon, and shape memory materials, such as poly(styrene-block-butadiene), polynorbornene, hydrogels, metallic alloys, and oligo($\epsilon$-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

Polylactide-co-glycolides (PLGA), as well as polylactides (PLA) and polyglycolides (PGA) have been used to make biodegradable implants for drug delivery. See U.S. Pat. No. 6,183,781 and references cited therein. Biodegradable materials have been developed for use as implantable prostheses, as pastes;, and as templates around which the body can regenerate various types of tissue. Polymers that are both biocompatible and resorbable in vivo are known in the art as alternatives to autogenic or allogenic substitutes. In a preferred embodiment, polymers are selected based on the ability of the polymer to elicit the appropriate biological response from cells, for example, attachment, migration, proliferation and gene expression.

Solvents for most of the thermoplastic polymers are known, for example, methylene chloride or other organic solvents. Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression.

For example, molds can be, coated with a unique temperature-responsive polymer, poly-N-isopropyl acrylamide (PNIPAAm), which demonstrates a fully expanded chain conformation below 32° C. and a collapsed, compact conformation at high temperatures. When grafted onto surfaces of silicon wafers using electron beam irradiation, it can be used as a temperature switch for creating hydrophilic surfaces below 32° C. and hydrophobic surfaces above 32° C. Since PNIPAAm is insoluble in water over the lower critical solution temperature (LCST about 32° C.) and reversibly solubilized below the LCST, cells detach from the substratum by simply lowering the temperature below the LCST. One of skill in the art can 1) engraft the polymer on silicon wafers that are pre-coated with polystyrene or 2) engraft the polymer on silicon wafers whose surface is first modified by vinyl-tricholorosilane. Either of these techniques will ensure that the polymer is better integrated and conjugated to its substratum (polystyrene in the former case and vinyl groups in the later case) so that it can serve as an effective thermal switch, useful in reversing cell attachment and detachment as a single contiguous layer of cells without the usual cell damage.

Another system for promoting both cellular adhesion and lifting of cells as intact sheets can involve the use of RGD (Arg-Gly-Asp) peptides. The RGD sequence is part of the domain within the fibronectin molecule that endows it with the ability to interact with adhesion molecules present on the cell surface of fibroblasts. Fibronectin itself is a well-characterized extracellular, structural glycoprotein which interacts strongly with other extracellular matrix molecules and which causes the attachment and spreading of most cells. This function of the fibronectin molecule is localized primarily to the RGD sequence. One of skill in the art can synthesize RGD peptides with a structural backbone of PMMA that has an RGD peptide sequence at its tips, bound to one another with the intermediate layering of polyethylene oxide. This allows differential cell adhesion in only selected areas and not others. Once the tissue of desired quality is formed, release of this intact monolayer of tissue from its substratum is straightforward; it requires only the addition of soluble RGD to the culture medium to act as a competitive substrate to the insolubilized RGD substrate on the silicon mold surface.

In some embodiments, attachment of the cells to the mold and/or polymer scaffold is enhanced by coating the substrate with compounds such as basement membrane components, agar, agarose, gelatin, gum arabic, types I, II, III, IV, and V collagen, fibronectin, laminin, glycosaminoglycans, matrigel, vitrogen, mixtures thereof, and other materials known to those skilled in the art of cell culture.

Thus, by the methods of the invention, cells can be grown on molds that are uncoated or coated as described herein, depending upon the material used for mold construction. Alternatively, cells can be grown on polymer scaffolds made by replica molding techniques.

Design of Apparatus

In a preferred embodiment, as shown in FIG. 3A, mold and/or polymer scaffold pieces are fitted together and optionally separated by a semi-permeable membrane. The vascular cells can be seeded into one layer and cultured to form vascular channels based on the pattern etched in the surface of the mold. Organ or tissue specific cells can be added to the second patterned surface, where they attach and proliferate to form a vascularized tissue bilayer. The second patterned surface optionally comprises inlets for neural inervation, urine flow, biliary excretion or other activity.

Figure 4:
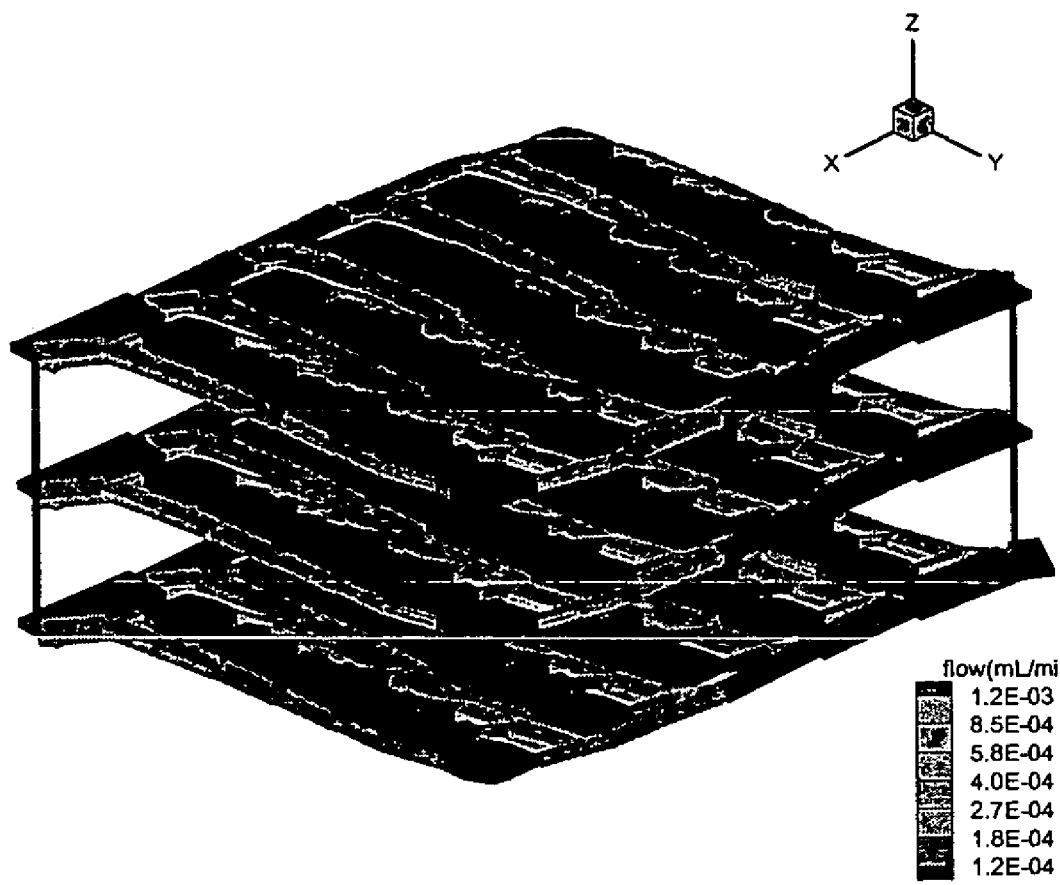
FIG. 4 shows a three-dimensional configuration, prepared according to methods known in the art, having only one inlet and outlet channel for integration of the network. These techniques use a single vertical link between 2D networks at the largest vessel diameter for the inlet and outlet, resulting in alternating horizontal sheets of vessels and unpatterned polymer stacked in the vertical dimension.
Figure 5:
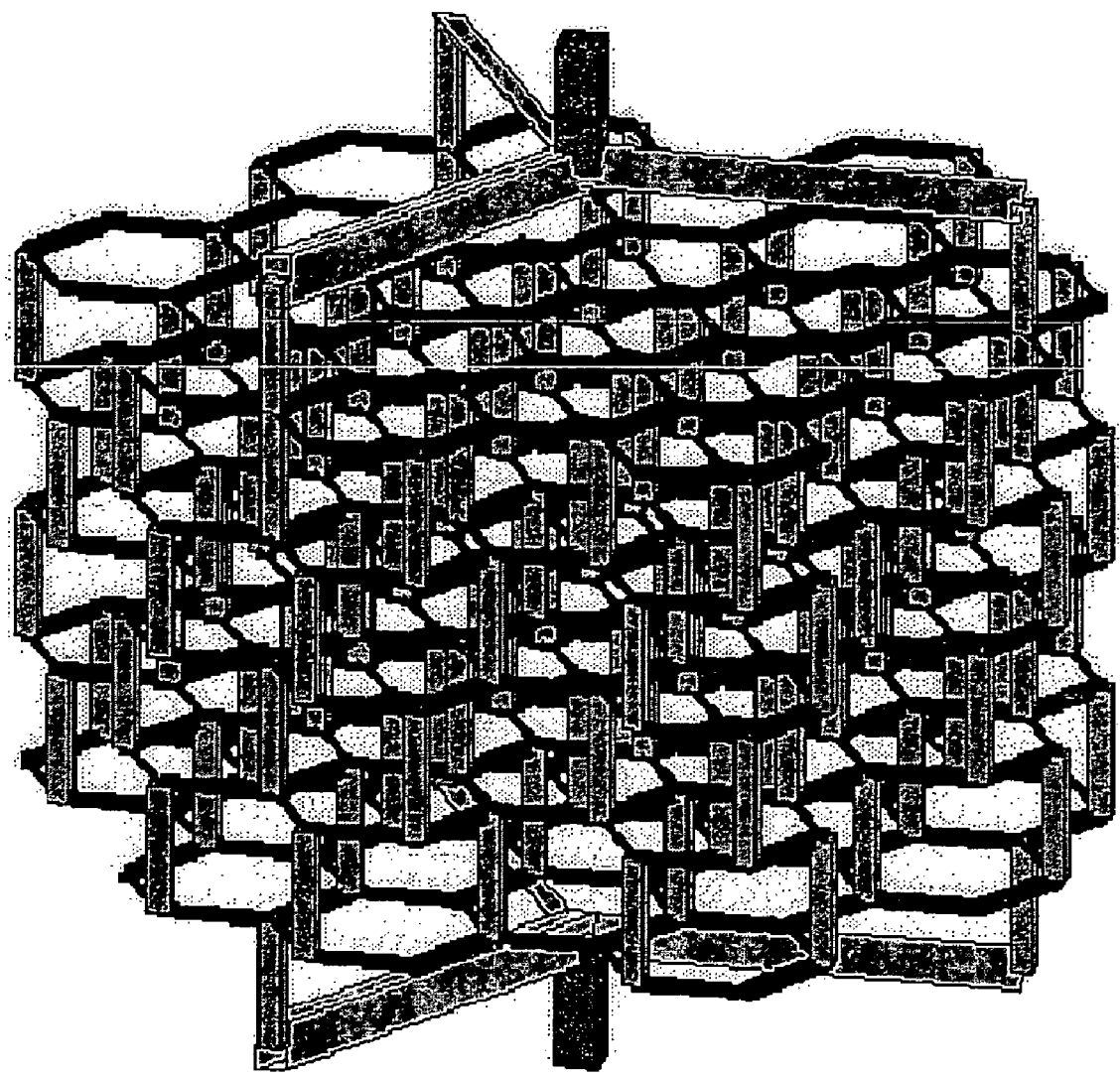
FIG. 5 shows a three-dimensional network designed using methods of the present invention, having a very large number of vertical interconnects between layers, in contrast to FIG. 4.
Figure 6:
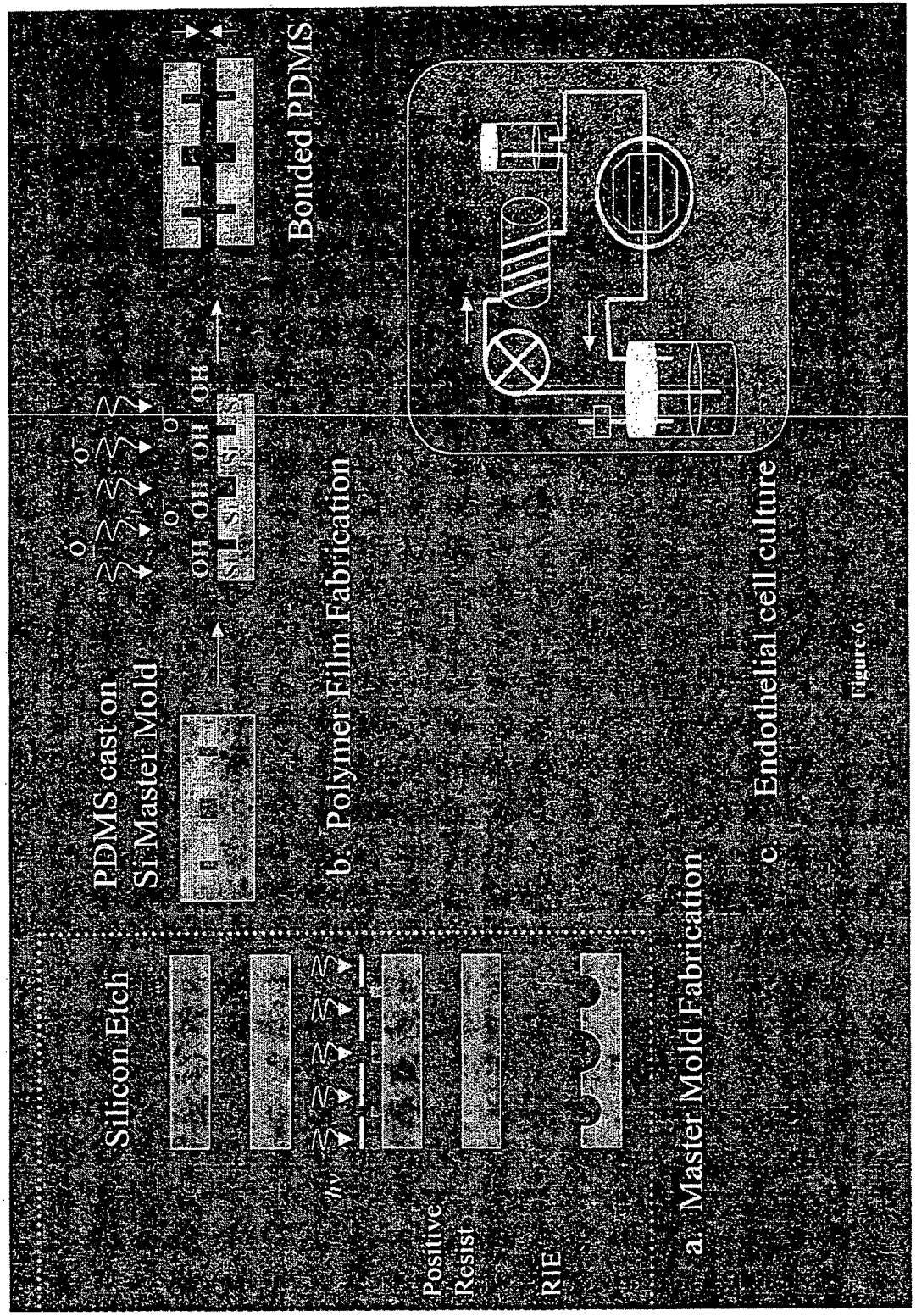
FIGS. 6A, B and C show schematics of a process for making a tissue layer.

The present invention requires that a number of designs be incorporated into a matrix, with each design corresponding to a polymer layer arranged in a repeating pattern in three dimensions. Fabrication allows for multiple silicon master molds, each master mold with a different channel design with intervening through-hole layers, rather than having only inlet and outlet layers at opposing diagonal corners (FIG. 4), and has a much more complex and dense array of through-holes connecting large numbers of smaller vessels (FIG. 5).

System for Modeling and Designing Physiological Networks

A system for modeling and designing physiological networks according to the present invention may be embodied, in whole or in part, in a software program to be executed by a general purpose computing device and/or a specific purpose device having embedded instructions for performing tasks included in said system. For illustrative purposes, the invention will be described as embodied in software programs executed using a general purpose computing device.

Figure 7:
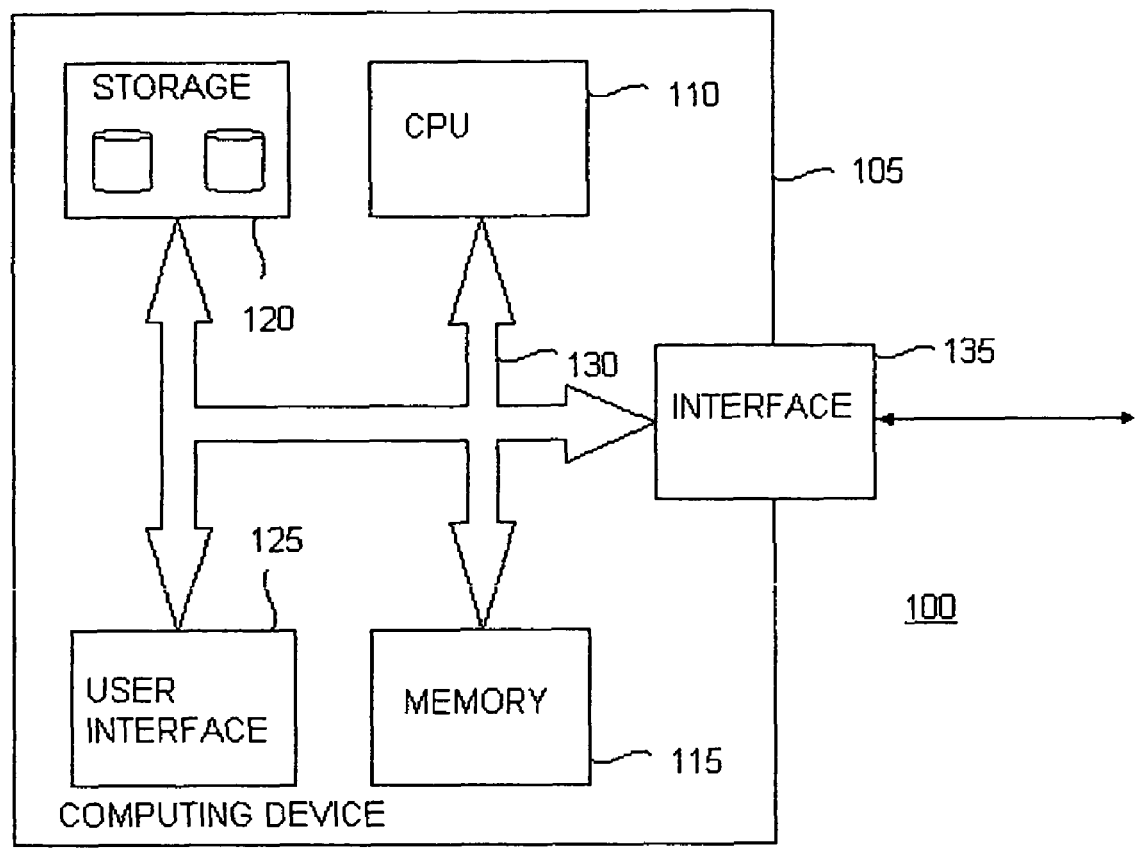
FIG. 7 is a diagram illustrating a system for designing and modeling fluidic networks in accordance with an embodiment of the invention.

FIG. 7 is a diagram illustrating a system configuration 100 in accordance with an embodiment of the invention. As shown in FIG. 7, system 100 may comprise a computing device 105, which may be a general purpose computer (such as a PC), workstation, mainframe computer system, and so forth. Computing device 105 may include a processor device (or central processing unit "CPU") 110, a memory device 115, a storage device 120, a user interface 125, a system bus 130, and a communication interface 135. CPU 110 may be any type of processing device for carrying out instructions, processing data, and so forth. Memory device 115 may be any type of memory device including any one or more of random access memory ("RAM"), read-only memory ("ROM"), Flash memory, Electrically Erasable Programmable Read Only Memory ("EEPROM"), and so forth. Storage device 120 may be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 120 may also include a controller/interface (not shown) for connecting to system bus 130. Thus, memory device 115 and storage device 120 are suitable for storing data as well as instructions for programmed processes for execution on CPU 110. User interface 125 may include a touch screen, control panel, keyboard, keypad, display or any other type of interface, which may be connected to system bus 130 through a corresponding input/output device interface/adapter (not shown). Communication interface 135 may be adapted to communicate with any type of external device, system or network (not shown), such as one or more computing devices on a local area network ("LAN"), wide area network ("WAN"), the internet, and so forth. Interface 135 may be connected directly to system bus 130, or may be connected through a suitable interface (not shown).

While the above exemplary system 100 is illustrative of the basic components of a system suitable for use with the present invention, the architecture shown should not be considered limiting since many variations of the hardware configuration are possible without departing from the present invention. As described above, system 100 provides for executing processes, by itself and/or in cooperation with one or more additional devices, that may include programs for modeling and designing physiological networks according to flow parameters in accordance with the present invention. System 100 may be programmed or instructed to perform these processes according to any communication protocol, programming language on any platform. Thus, the processes may be embodied in data as well as instructions stored in memory device 115 and/or storage device 120 or received at interface 135 and/or user interface 125 for execution on CPU 110. Exemplary processes for carrying out the invention will now be described in detail.

Overview of Design Method

Software tools executed on system 100 may be used to design fluidic networks appropriate for use as vasculatures in tissue engineered organs. A fluidic network may be considered appropriate for use in tissue engineered organs if the network mimics vital behavior of natural vasculatures. Two kinds of measurable data on blood vessel networks in nature may be used for evaluating a fluidic network: measurements of the geometry of blood vessels, and measurements of the blood flow behavior in the vessels. Measurements of the geometry of the blood vessels may include vessel diameters, vessel lengths, and the branching pattern of the network. Measurements of the blood flow behavior may include flow velocities, fluidic pressures, and forces exerted by the fluid shearing against the vessel wall.

The flow behavior in a single blood vessel may be modeled by a single equation. The equation used may vary depending on the type of vessel and type of fluid in question. A network of blood vessels may be modeled by a system of equations, where each vessel is represented by a single equation. There may be overlap in the equations: for example, if two vessels are connected, the amount of fluid flowing through one (the flow rate) will equal the amount of fluid flowing into the other. The equations are thus interrelated, and this type of system is known as a system of "simultaneous" equations. More equations may be added to the system to represent constraints on the network, such as requiring that two vessels have the same flowrate. Thus, a fluidic network having thousands of individual vessels may be described by a system of thousands of simultaneous equations.

In accordance with an embodiment of the invention, a software program for use with system 100 may include steps as follows: receiving a branching pattern, indicating how many vessels there are, how they are connected to each other, and how large the tissue or organ supported by the fluidic network is. The system may set up an equation for each vessel, keeping track of how the equations are related to each other. The system may need more information to solve all of the equations. If the geometry is provided to the system, indicating the length and diameter of each vessel, the software can solve the system and determine the flow behavior throughout the network. Furthermore, with flow velocities and pressure, the software can solve the system and provide an optimal diameter for each vessel.

Figure 8:
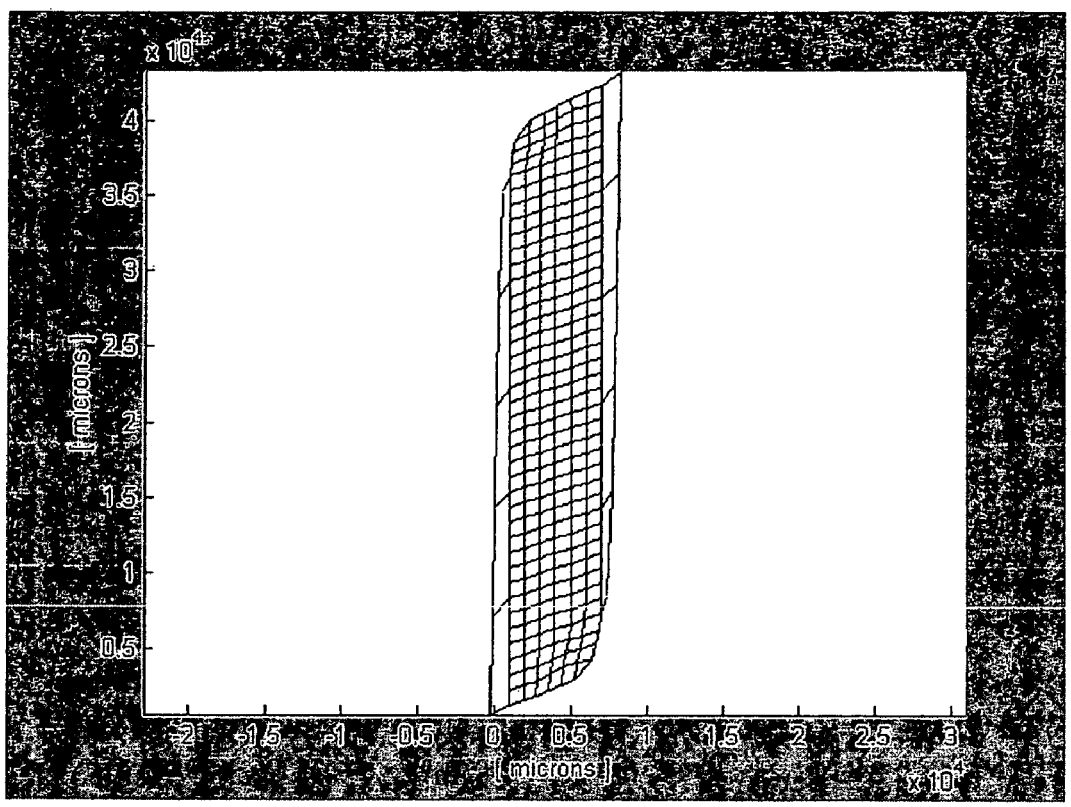
FIG. 8 illustrates a network, Testnet-0, designed in accordance with an embodiment of the invention.

In accordance with an embodiment of the invention, a combination of geometry and flow behavior may be used: for a branching pattern, flow may be distributed evenly throughout the network; and limits on the pressures and flow rates may be placed on the network. FIG. 8 illustrates a network designed using this method.

The technique described above accounts for each vessel by a single equation and the entire system of equations can be solved at once. The single equation for each vessel assumes that the fluid in the vessel is behaving as a simple fluid. Blood, however, may be modeled as something other than a simple fluid: cells and other materials that affect flow properties may also be taken into account.

Therefore, in accordance with an embodiment of the invention, a program may be provided to accurately model the flow of blood in networks and to account for these factors. Including these effects expands the system of equations from thousands of equations to hundreds of thousands of equations, and advanced techniques may be required to solve a system of this size.

Physiological Network Topology

In a blood vessel network, vessels larger than ~20 μm in diameter may show a treelike topology. That is, a large vessel may divide into two or more smaller vessels. Blood vessels smaller than ~20 μm, including the capillaries, may be arranged in bundles, where a number of vessels of the same size are interconnected. The topology of a vasculature network can be described using a numbering system. In accordance with an embodiment of the invention, a diameter-defined Strahler ordering system can be used (Jiang et al., Journal Of Applied Physiology 76 (2):882 (1994), the contents of which are incorporated herein by reference). In this system, vessels may be given order numbers, where the smallest vessels are order 0 and the larger vessels have higher numbers. Useful information can be extracted from the ordered network, such as which order vessels are likely to be connected to each other and how many vessels of each order exist in the network.

Physiological Flow Behavior

There are several properties the flow through a vasculature may need to satisfy in order to support a living organ. Basic requirements of a vascular network may include:

1. allowing cells to be seeded on the inside of the vessels;
2. providing nutrient transport to and from all parts of the tissue being supported; and
3. being able to be implanted without disturbing blood flow to other organs.

From each basic requirement more specific required characteristics of the network can be derived:

1. The process of seeding cells on the inside of the vessels and the behavior of those cells may be highly dependent on the shear stresses applied by the fluid at the wall. A network may be generated such that the shear throughout the network is constant to give uniform seeding and growth. This is consistent with hypothetical and experimental investigations of physiological vasculature.
2. The network may include a sufficient number of vessels distributed throughout the volume of the tissue to provide nutrient transport throughout the organ. The distribution of various-sized vessels has been measured in numerous physiological systems, and a network may be generated to match the physiological distribution.
3. The network may be generated such that conditions at the boundary match those of the network being replaced, thus allowing implantation without disturbing blood flow to other organs. The boundary conditions are the pressure drop across the network and the total flow rate through the network. These values have been measured for various organs in numerous animals.

A vasculature design satisfying the above-listed criteria may be used to support a living organ.

Device Topology Design

The first step of designing a fluidic network is to specify a network topology. Networks may be described using a node-vessel form often used to describe networks of electrical resistors. This format may consist of a list of nodes and a list of vessels. In the list of nodes, an x, y, and z location is assigned to each node. For n nodes the list may be:

$$Nodes = \begin{vmatrix} 1 & x_1 & y_1 & z_1 \\ 2 & x_2 & y_2 & z_2 \\ & & \vdots & \\ n & x_n & y_n & z_n \end{vmatrix}. \quad (1)$$

A vessel connects two nodes, so in the list of vessels each vessel may be defined by the two nodes at its ends. For m vessels:

$$Vessels = \begin{vmatrix} 1 & node_{1a} & node_{1b} \\ 2 & node_{2a} & node_{2b} \\ & \vdots & \\ m & node_{ma} & node_{mb} \end{vmatrix}, \quad (2)$$

where $node_{ia}$ is the node at one end of vessel i and $node_{ib}$ is the node at the other end. Such a network may be created and manipulated in a programming environment on system 100, such as Matlab® and the like.

Figure 9:
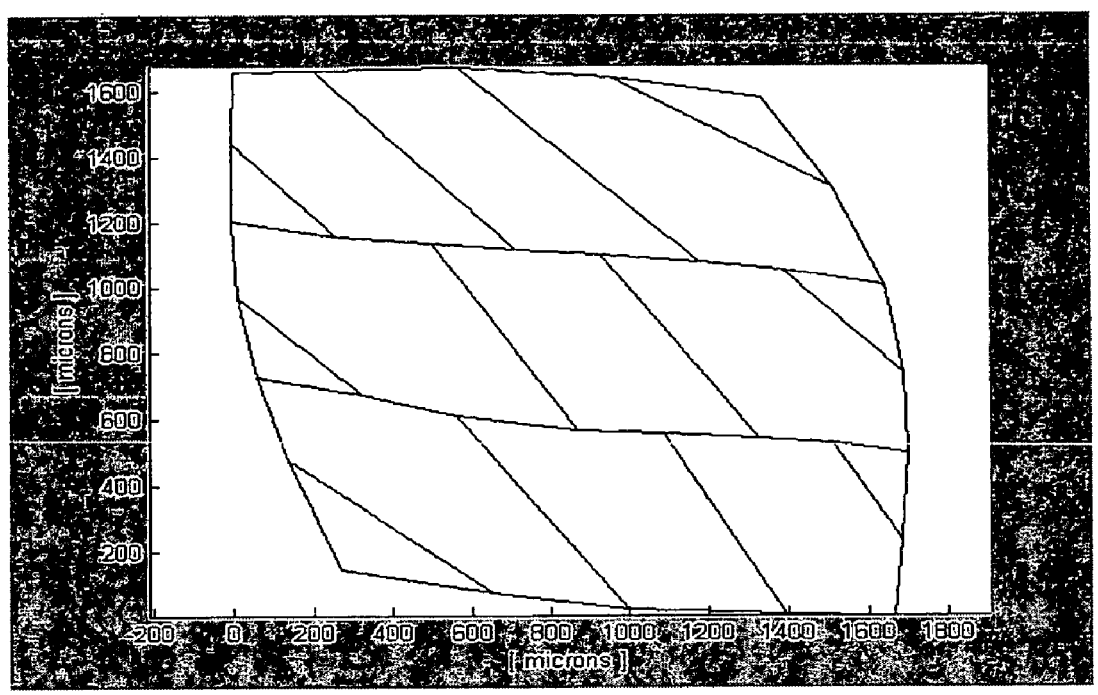
FIG. 9 is a diagram showing capillary bed topology for a network, Testnet-0, created using node-vessel data.

FIG. 9 is a diagram showing a network, Testnet-1, created by placing nodes on a grid and using an algorithm to connect selected nodes. The algorithm may count through all of the nodes on the grid and create vessels to connect each node to its nearest neighbors. Modifications may be made to the network by manually changing node locations and deleting some vessels.

A network may be created using a different method. A graphical user interface, for example, the Matlab® interface, may be used to create a drawing program. Lines drawn by a user are recorded in node-vessel format. Each time a new line is drawn the distances between its endpoints and all other existing endpoints are measured. If the distance between any two points is short enough, they can be considered to be the same point.

Figure 10:
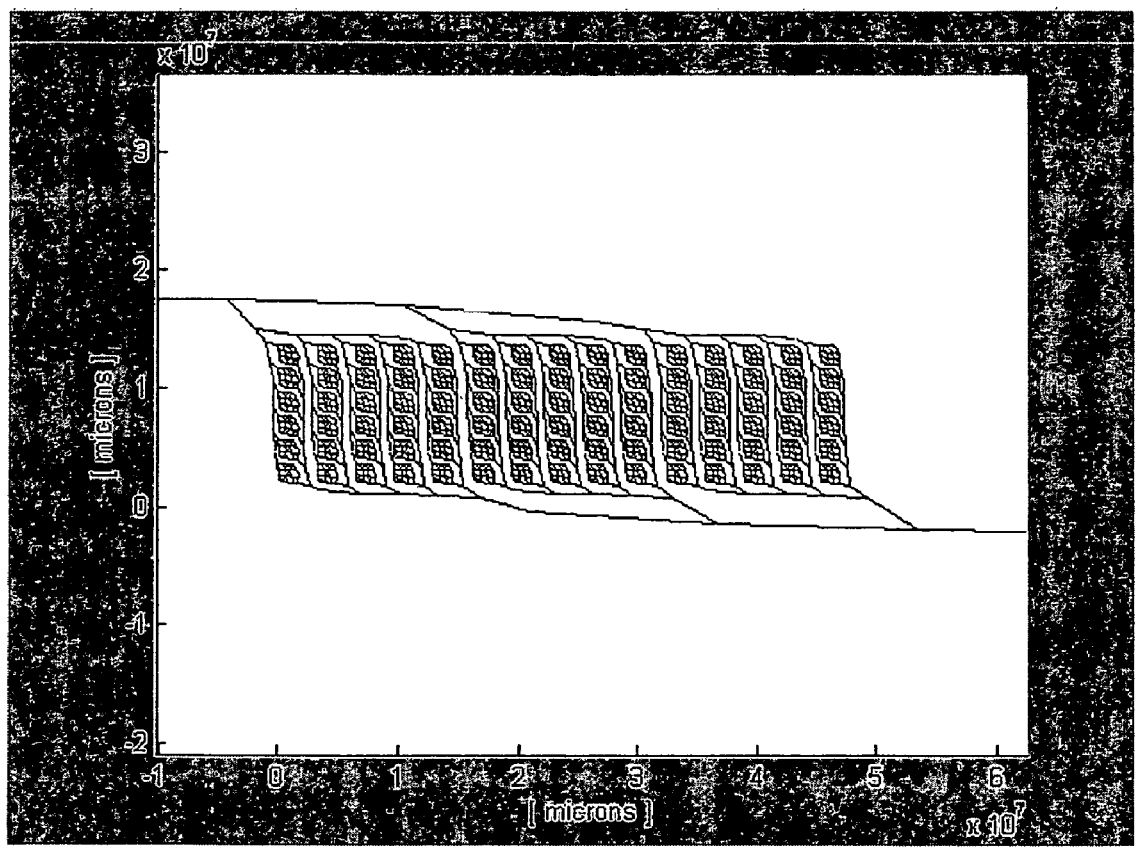
FIG. 10 is a diagram illustrating the topology of a network, Testnet-1, in accordance with an embodiment of the invention.
Figure 11:
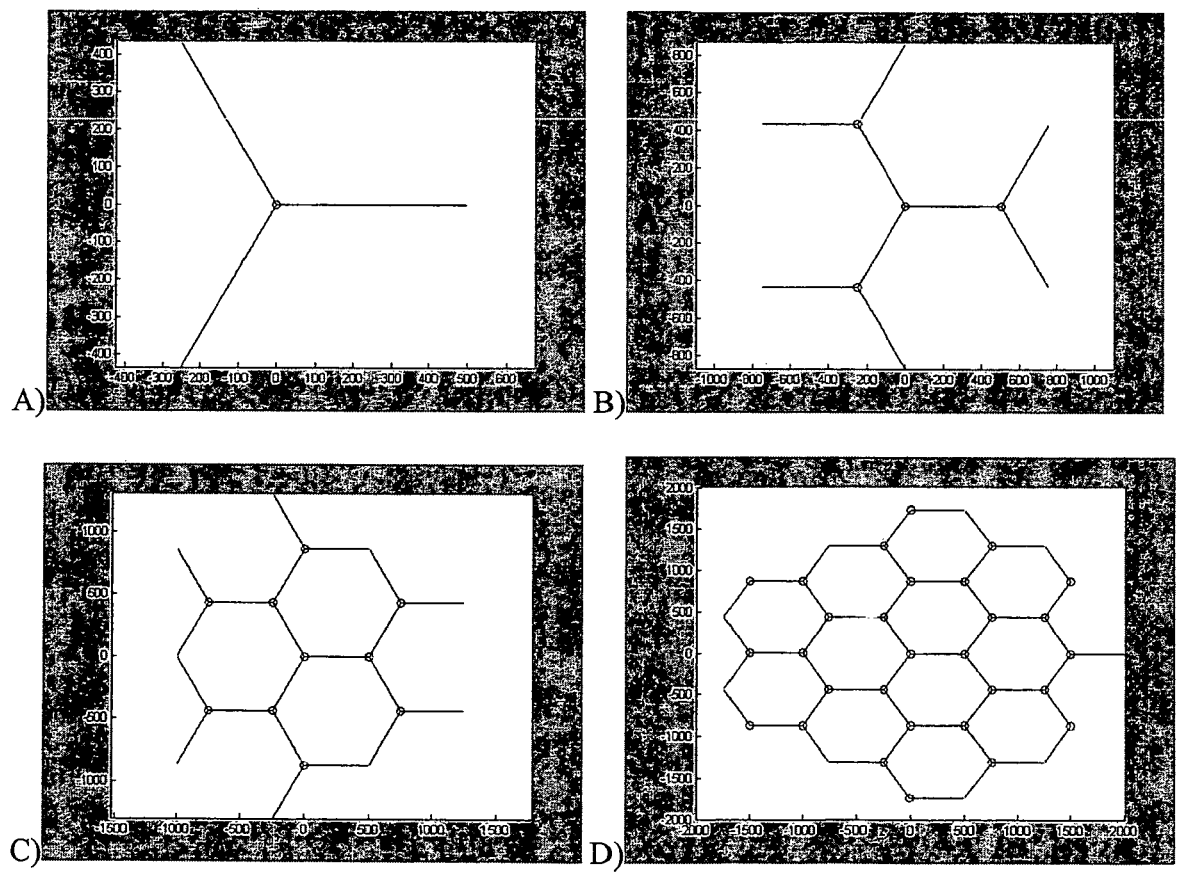
FIG. 11 illustrates a branching sequence in which a fractal algorithm was used to create a hexagonal pattern.

FIG. 10 is a diagram illustrating a network, Testnet-1, using this method.

This network was created to match the branching pattern of a physiological capillary bed. The network was then multiplied over a larger area and more connections were drawn in, creating the full topology of the design shown in FIG. 10.

The topography of a three-dimensional stacked design may be based on a fractal algorithm. This algorithm was chosen because it can be used to create patterns of any size with the vessels spaced evenly throughout, and avoids sharp angles between intersecting vessels. The algorithm may include steps as follows:
1. Define a reference direction in the plane.
2. Define a vessel length L.
3. Define an origin.
4. Define a maximum pattern diameter.
5. Create three vessels with one node at the origin, each length L: one extending parallel to the reference direction, one at 120° from the reference direction, and one 240° from the reference direction.
6. Iterate through all of the newly created nodes. At each node, redefine the reference direction as the direction of a vessel connected to that node, redefine the origin as the current node, and perform step 5.
7. Repeat steps 5 and 6 until no new nodes can be added within the maximum pattern diameter.

Figure 18:
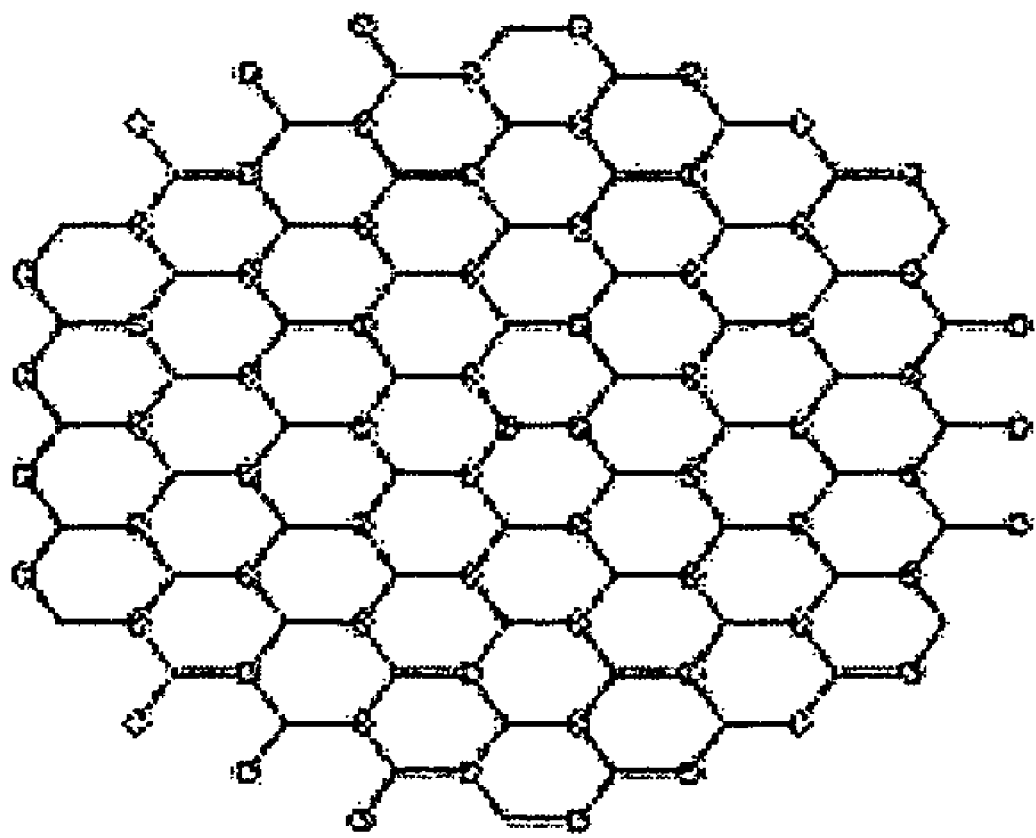
FIG. 18 shows a two-dimensional pattern produced by a fractal algorithm in accordance with an embodiment of the invention.
Figure 19:
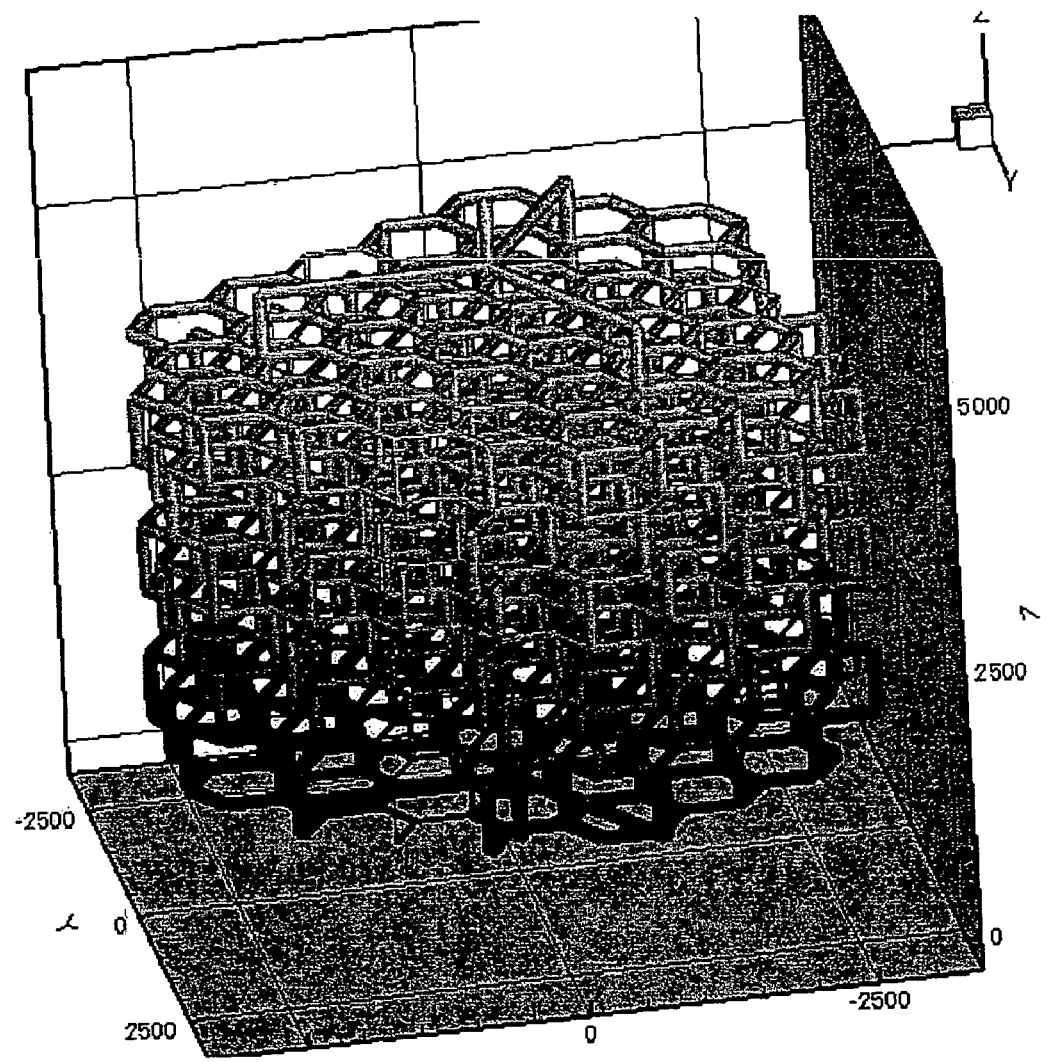
FIG. 19 shows a sample initial network in accordance with an embodiment of the invention.

A two-dimensional pattern produced by this algorithm is shown in FIG. 18. A three-dimensional network may be generated by stacking a set of two-dimensional layers. Layers in the middle of the pattern may be identical, while layers on the outside may be less dense to act as distribution layers. The software may search through all nodes in the network, connecting each pair of nodes that are found on adjacent layers and are aligned vertically. Inlet and outlet vessels may be added to either end, completing the initial network. A sample initial network is shown in FIG. 19.

Figure 12:
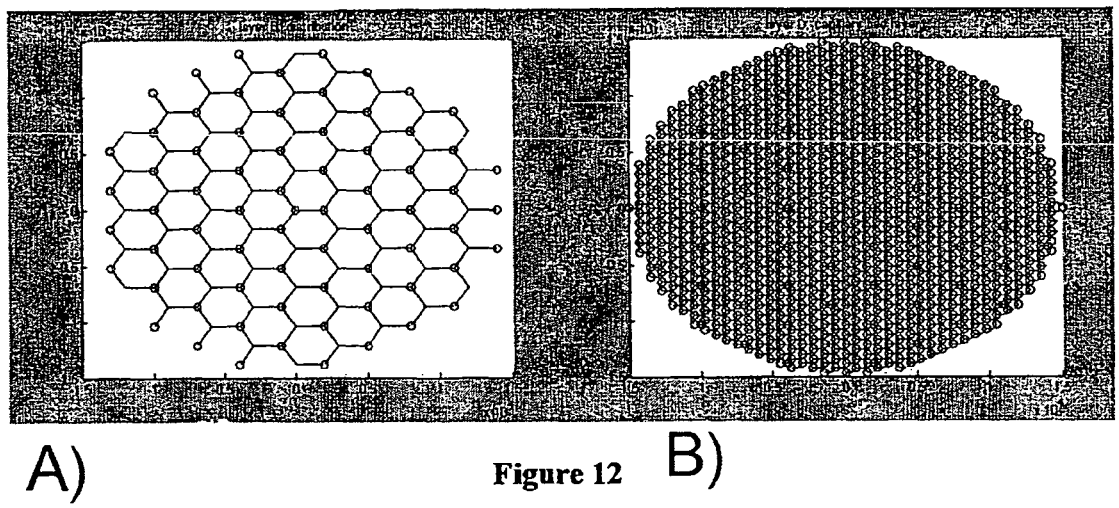
FIG. 12 illustrates a three-dimensional design, Hextak, in accordance with an embodiment of the invention. The layers in Hextak contain vessels in the plane of the wafer. Black lines mark vessels in the plane of the wafer; red and blue circles mark locations where vertical vessels meet these patterns.
Figure 13:
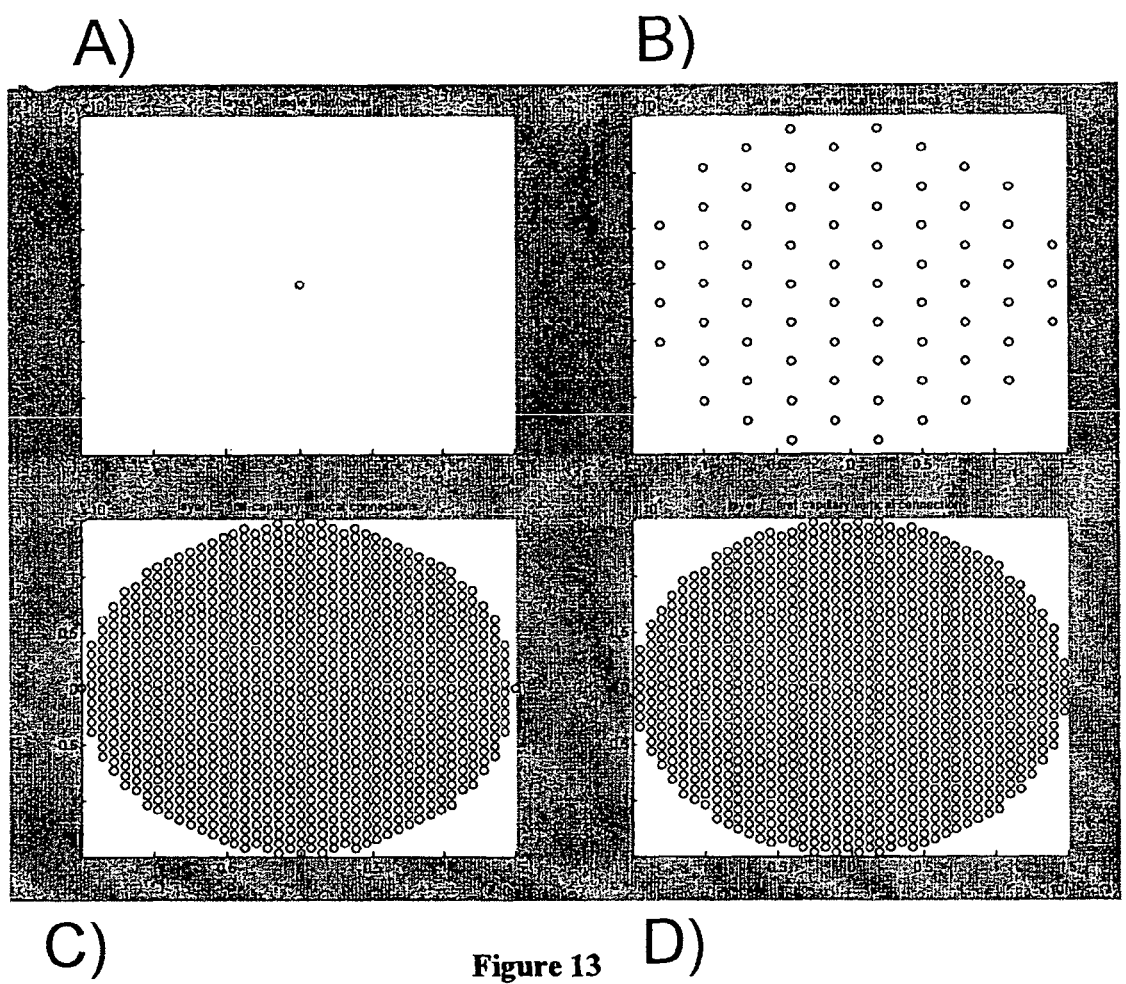
FIG. 13 illustrates four separate layers of vertical vessels in the Hextak design.

FIG. 12 illustrates a three-dimensional design, referred to here as "Hextak." As shown in FIG. 12, a series of vessel layers may be laid out on different wafers. The vessels in various layers may be interconnected by a pattern of vertical vessels. These vertical vessels are added to the design by placing them at regular distances throughout the patterns and are also shown in FIG. 12. The Hextak design may include four separate layers of vertical vessels, as shown in FIG. 13. A method for this Hextak design will be described in further detail below.

The above-described methods create a network topology and describe it in node-vessel format. The node-vessel format may then be used to model the fluidic behavior in the network.

Predicting Flow Through a Single Microfabricated Vessel

The flow behavior and geometry of a cylindrical blood vessel can be related by a single equation, $$\mu \frac{Q}{\Delta P} = \frac{\pi D^4}{128L}, \quad (3)$$

where Q is the flow rate through the vessel, $\mu$ is the viscosity of the fluid flowing through the vessel, $\Delta P$ is the pressure drop in the vessel, D is the diameter of the vessel, and L is the length of the vessel. The terms on the left-hand side of Equation (3) are representative of the flow behavior while the terms on the right-hand side are representative of the geometry of the vessel. Thus, if the geometry of a vessel is known, the flow behavior can be calculated and if the flow behavior is known, the geometry can be calculated.

The vessel can be described as a fluidic resistor, analogous to an electrical resistor. In this case the relation between flow rate and pressure drop may be given by $$\frac{\Delta P}{Q} = R, \quad (4)$$

where R is the fluidic resistance of the vessel, which is dependent only on the geometry of the vessel and the viscosity of the fluid. Equations 3 and 4 can be rearranged to find the resistance of a cylindrical vessel $$R_i = \frac{8\mu L}{\pi D^4} \quad (5)$$

Similar equations for various non-cylindrical vessels, including etched vessels, may also be used. The flow in a lithography-etched vessel may be accurately predicted by the relation for flow in a rectangular vessel $$\Delta P = \frac{\mu L(x+y)^2}{8(xy)^3}\left(96 - 95\left(\frac{x}{y}\right) + 56\left(\frac{x}{y}\right)^2\right)Q, \quad (6)$$

where $\Delta P$ is the pressure drop from one end of the vessel to the other end, $\mu$ is the viscosity of the fluid flowing through the vessel, L is the length of the vessel, x is the width of the vessel, y is the depth of the vessel, and Q is the flow rate through the vessel.

Combining Equations (4) and (6) gives the expression for the fluidic resistance of a vessel:

$$R = \frac{8(xy)^3}{\mu L(x+y)^2}\left(96 - 95\left(\frac{x}{y}\right) + 56\left(\frac{x}{y}\right)^2\right)^{-1} \quad (7)$$

Predicting Flow through a Network of Vessels

As a single vessel can be modeled by a fluidic resistor, a network of vessels can be modeled by a network of resistors (i.e. an electric circuit). Thus, methods for analyzing electrical resistor networks may be used for analyzing analogous fluidic networks.

The node-vessel topology can be translated into a set of equations describing the flow behavior in the network. The first network calculation is to find the flow rates throughout the network. Since it is desirable to have the flow throughout a network be evenly distributed, vessels may be designated as capillaries in size and a flow rate for each may be assigned accordingly. The flow rates may be stored in a list where each vessel has a corresponding flow rate. The equation for continuity in fluidic networks, or the analogous Kirchoff Current Law in electrical circuits, tells that the sum of all flow rates at any node in the network is zero. As long as enough capillaries are defined, this law may be used to find the flow rates throughout the network. The software goes through the list of nodes calculating flow rates at every node that it can. For example, if a node has three vessels connected to it and two of those vessels have known flow rates, the flow rate in the third vessel can be found. Thus, the flow rates of all of the vessels in the network may be determined.

Once all the flow rates are known, a system of equations describing the flow behavior in the network can be created. The network where the pressures and resistances throughout the network are unknown may be described by a set of simultaneous linear equations. In matrix form, $$\begin{bmatrix} [N] & [Q] \\ & [K] \end{bmatrix} \begin{bmatrix} \overline{P} \\ \overline{R} \end{bmatrix} = \begin{bmatrix} \overline{0} \\ \overline{k} \end{bmatrix}, \quad (8)$$

where [N] is a matrix that picks values out of the pressure vector to go in the element equations, [Q] is a diagonal vector with entries corresponding to the flowrate in each vessel, $\overline{P}$ is the vector of unknown pressures, $\overline{R}$ is the vector of unknown resistances, [K] is a matrix of values representing the constraint equations, $\overline{0}$ is a vector of zeros, and $\overline{k}$ is a vector of known values.

The upper section of Equation (8), $$[[N][Q]]\begin{bmatrix} \overline{P} \\ \overline{R} \end{bmatrix} = [\overline{0}], \quad (9)$$

represents a set of Equation (4)'s, one for each vessel. This set of equations is set up by counting through the list of vessels, representing the two nodes at the end of each vessel in [N], and representing the flow rate in each vessel in [Q].

The bottom section of Equation (8), $$[K]\begin{bmatrix} \overline{P} \\ \overline{R} \end{bmatrix} = [\overline{k}], \quad (10)$$

represents the constraint equations. The system cannot be solved unless the number of rows in the matrix on the left-hand side of Equation (8) is equal to the number of pressures plus the number of resistances, i.e. there are n equations and n unknowns. Equation (9) supplies a number of rows equal to the number of resistances, so Equation (10) may be used to supply a number of rows equal to the number of pressures, also equal to the number of nodes in the system. The constraint equations can set pressures or resistances to constant-values, or set relationships between resistances or relationships between pressures, or any combination. The pressure at the inlet and outlet of the network may always be set to constant values in accordance with physiological requirements. Other relations may be to set pressure fronts where groups of nodes have the same pressure, or to set resistance groups, such as forcing all capillaries to have the same resistance. Some sets of constraints do not yield a solution, but others are guaranteed to always have a solution as long as reasonable numerical values are placed on the constraints. One of these sets is to constrain all of the pressures in the network and solve only for resistance.

Equation (7) is asymmetric and must be solved using Sparse Gaussian Elimination. The result is a list of the pressures and resistances throughout the network. When the resistances are known and an etch depth for each layer is specified, Equation (7) can be used to find the width of each vessel. Equation (7) cannot be solved explicitly for the width given the value of R, so a Newton Method may be used to solve Equation (7) for the width. Once the width of each vessel is known, the design is complete; the orientation and shape of all vessels in the network is known.

Figure 14:
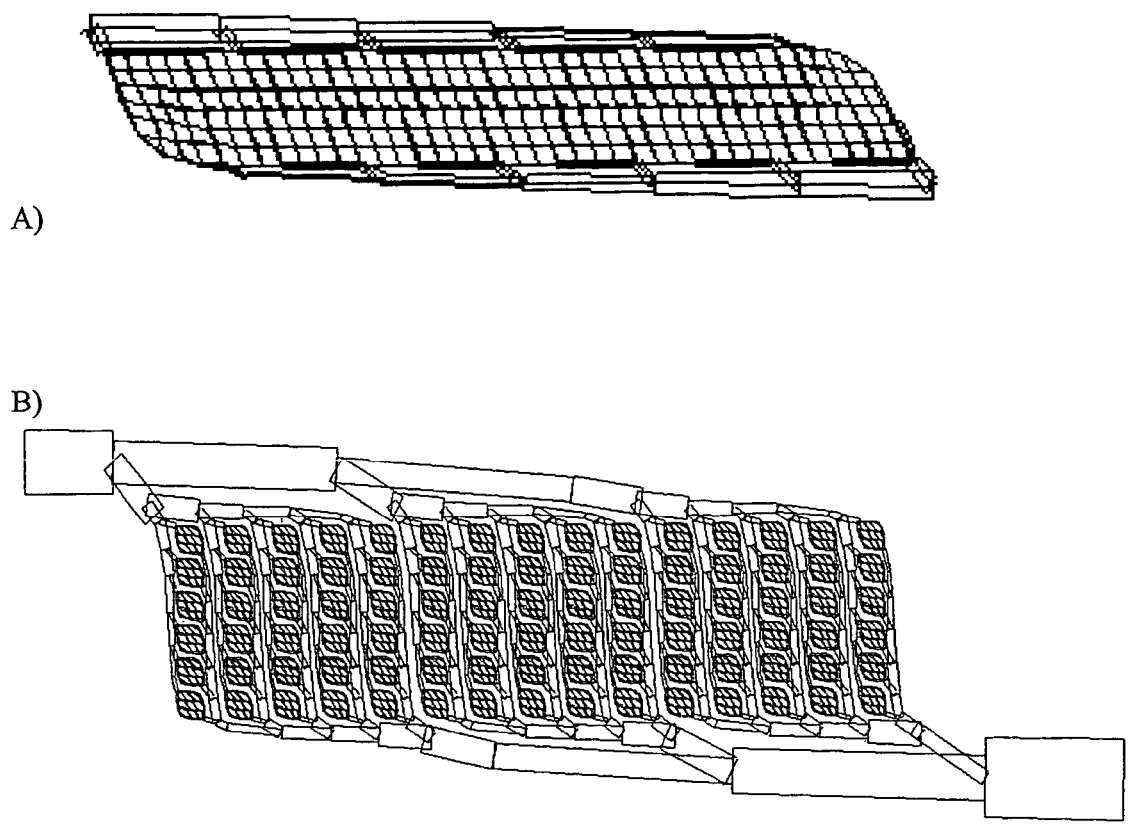
FIG. 14 is a diagram showing the schematics of the completed two-dimensional network designs for Testnet-0 (FIG. 14A) and Testnet-1 (FIG. 14B).
Figure 15:
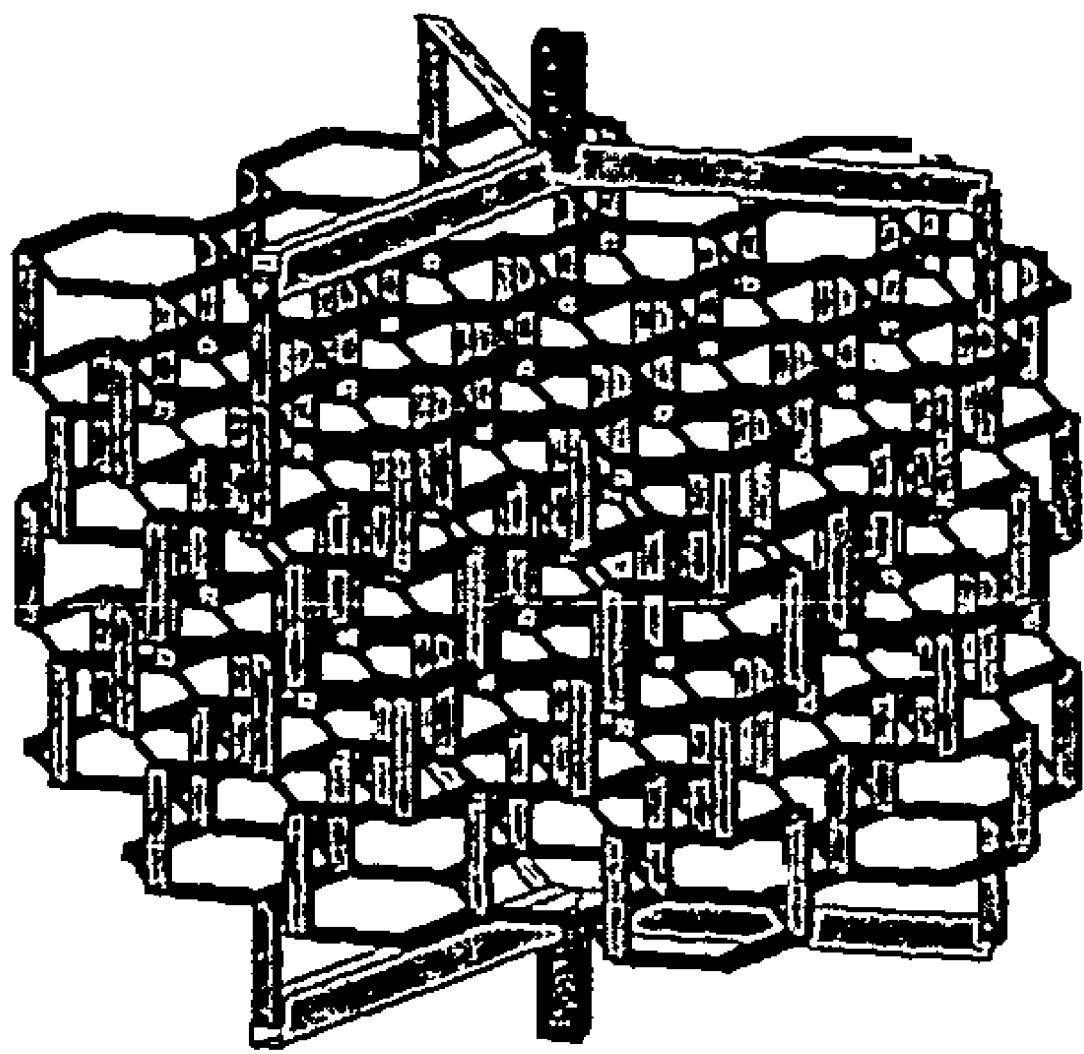
FIG. 15 is a diagram of a section of Hextak where each vessel is plotted as an individual three-dimensional element.

Schematics of the completed designs for Testnet-0 and Testnet-1 are shown in FIG. 14. FIG. 15 is a diagram of a section of Hextak where each vessel is plotted as an individual three-dimensional element.

Experimental Verification of Fluidic Model

Figure 16:
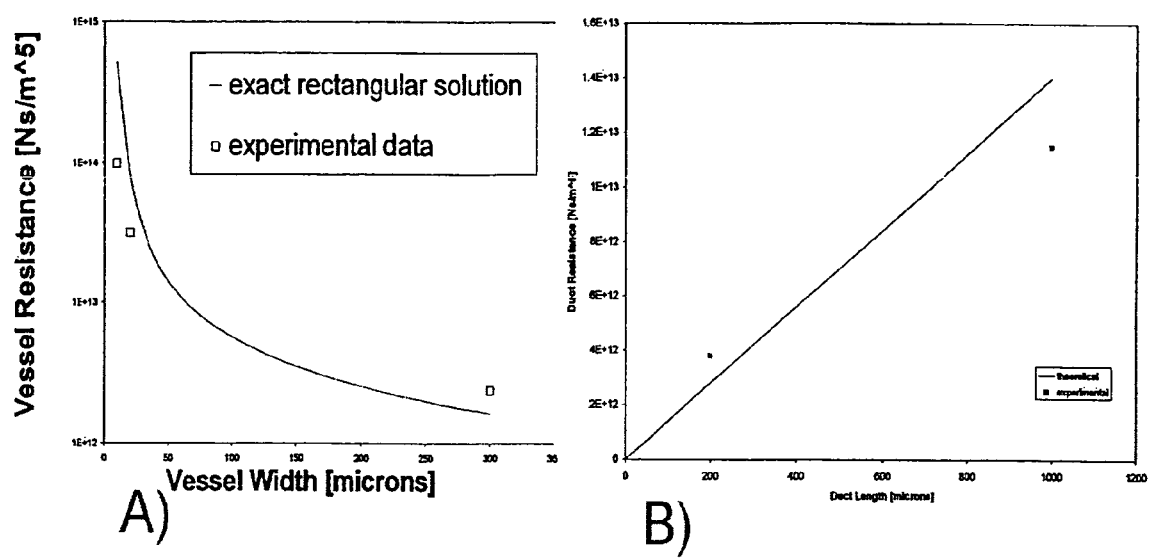
FIG. 16 shows fluidic resistance of vessels with varying widths (FIG. 16A) and varying lengths (FIG. 16B).

The model of flow in a single vessel and predictions of flows in small patterns have been shown to be accurate by measuring the flow rates through individual vessels and small patterns. An example from this work is presented in FIG. 16, showing the ability to predict the fluidic resistance of vessels with varying widths or varying lengths. The model was also shown to be accurate in small patterns in predicting flows at varying pressures and flow rates through vessels of varying depths and topology.

Figure 17:
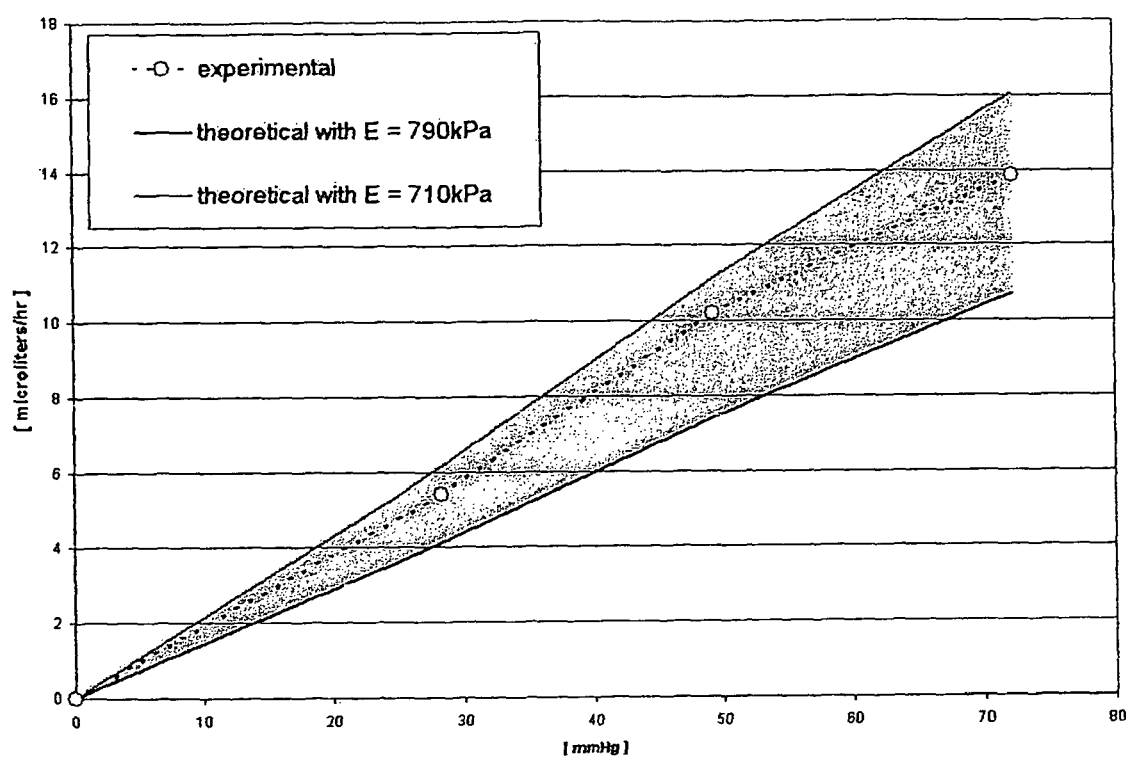
FIG. 17 is a diagram showing a comparison of the prediction made by the network modeling software to experimental data for the total flow rate through the vessel versus the pressure drop across the device for a Testnet-1.

The theoretical model has been shown to accurately predict gross behavior of full networks. As shown in FIG. 17, the model predictions match the experimental behavior within an acceptable error for variation in the elasticity of the material used to construct the network.

Implementation of Design Method

The design method may be implemented in any programming language, such as the C programming language and so forth. Programming code may be compiled using the GNU compiler collection. As described before, system 100 may include any general purpose computing device. For example, compiling and computation 10 may be performed on an SGI Origin 2000 workstation. Graphics maybe plotted using Matlab, Tecplot, or the like.

In accordance with an embodiment of the invention, the design method may include steps as follows:
1. Generate a network topology in Node-Vessel format using a fractal method.
2. Generate the system of flow equations (Equation 9).
3. Set the system of constraint equations (Equation 10).
4. Solve all of the equations (Equation 8) simultaneously to determine the vessel resistances.
5. Use the resistance-geometry relation (Equation 4) to determine the geometry of each vessel.

Figure 20:
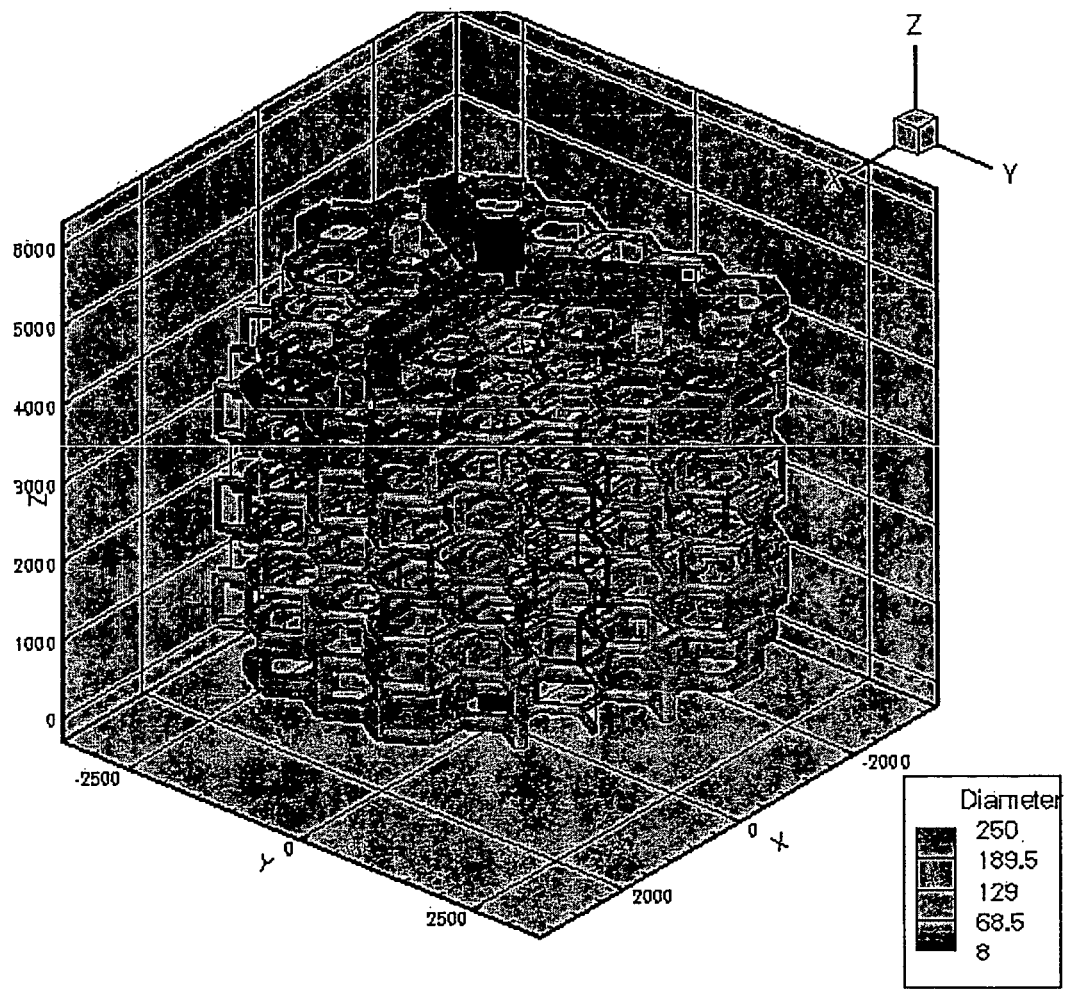
FIG. 20 depicts a full version of the design as shown in FIG. 5.

A full network appropriate for use as support for a tissue engineered organ is shown in FIG. 20.

Comparison of Network Designs to Physiological Systems

Once a network design has been completed, the Strahler ordering system can be applied to compare the network to physiological data. For the diameter-defined Strahler system, the diameter distribution of a designed network may match that of measured physiological systems. Flow properties may be used as inputs to the design so that the flow properties throughout the network also match physiological values. The number of vessels of each order may be compared. Mass transport occurs in the smallest vessels, so a network must have the appropriate number of small vessels to viably support an organ. A highly interconnected stacked device such as the Hextak provides the necessary number of vessels.

Figure 21:
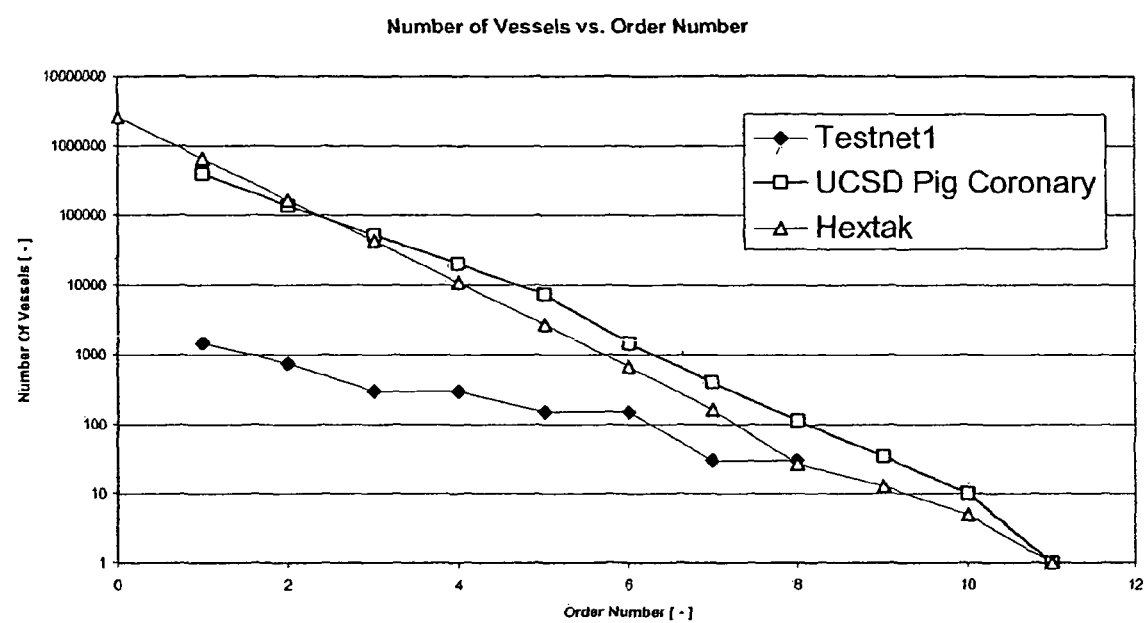
FIG. 21 shows the number of vessels of each order for a stacked Testnet-1, a Hextak, and a pig coronary arterial system.
Figure 23:
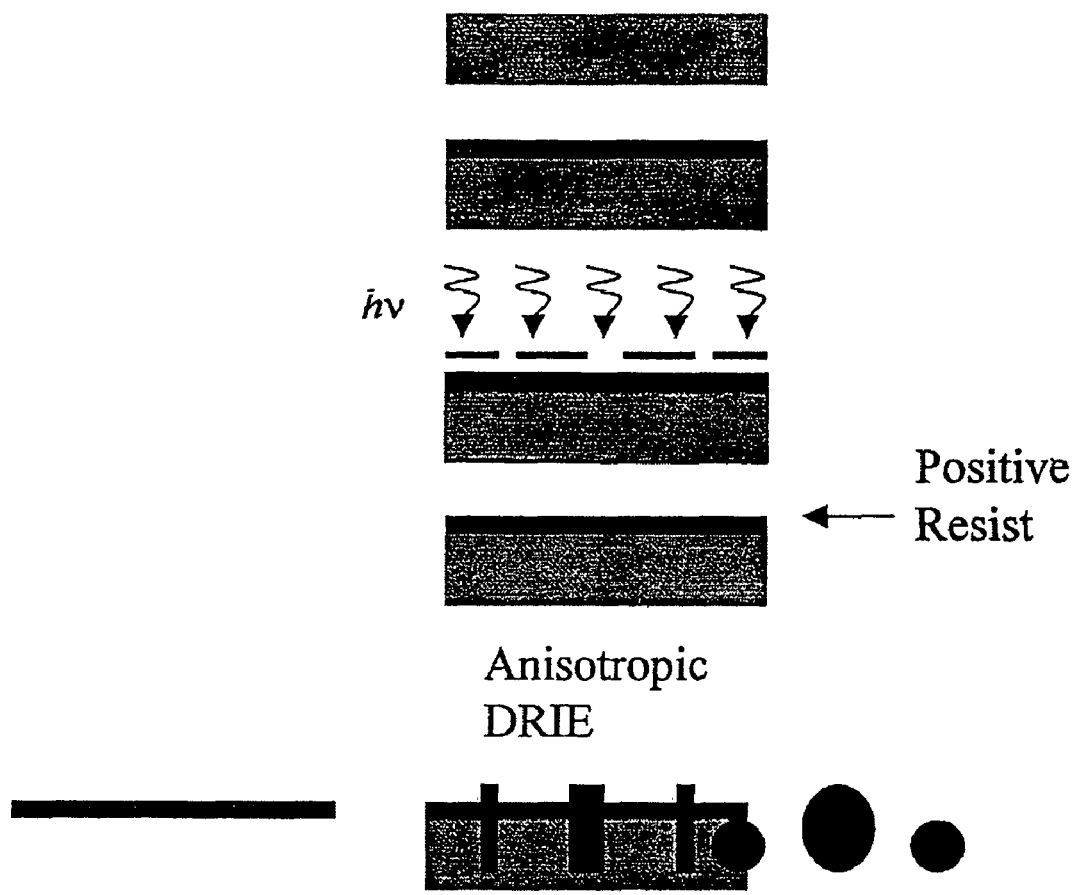
FIG. 23 shows a schematic of a pattern etched using an inductively-coupled plasma (ICP) system.
Figure 24:
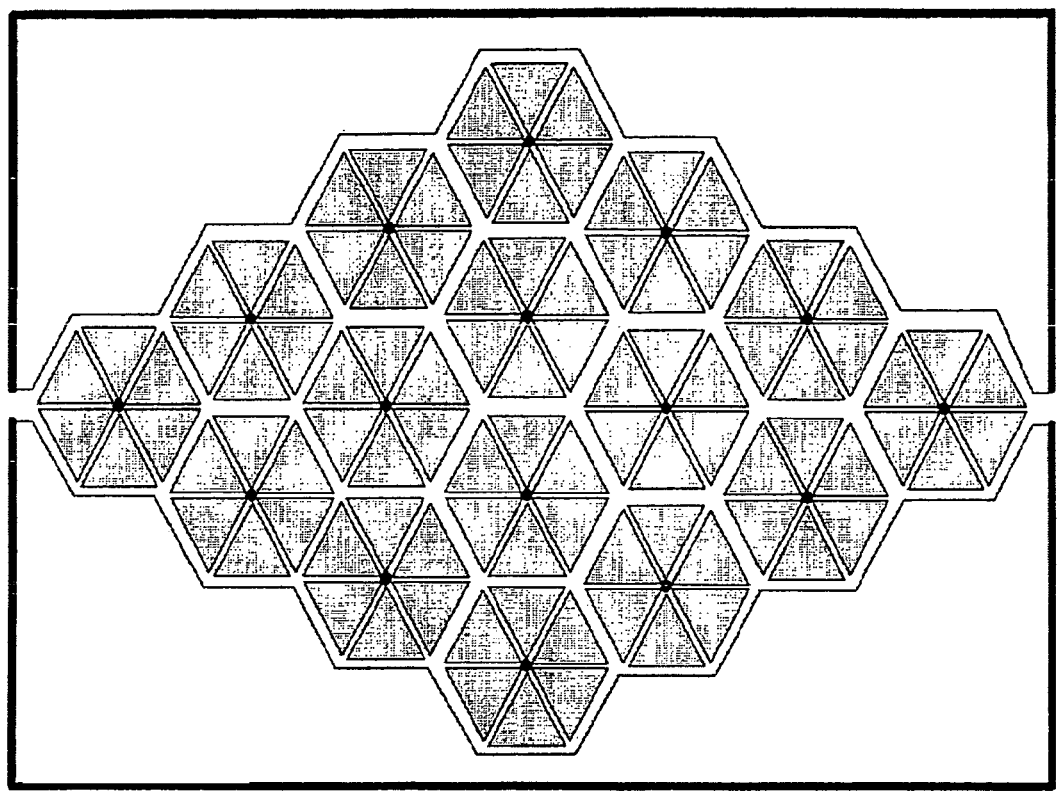
FIG. 24 shows a schematic top drawing of a mold or polymer scaffold. The triangles represent areas coated with cell adhesion molecules to promote the adhesion of cells. The white areas between the triangles represent microchannels; in some applications, they are not coated with cell adhesion molecules, and so are open for colonization by cells that can form vascular tissue. The black circle in the middle of each hexagon is a vertical through-hole.

FIG. 21 shows the number of vessels of each order for a stacked Testnet-1, a Hextak, and a pig coronary arterial system. The Hextak matches the physiologically appropriate number of vessels through all orders of vessels, including the smallest.

The invention comprehends the transmission of information, e.g., vessel geometry, flow characteristics, shear stresses, and so forth, from any of the herein methods, algorithms, or applications thereof; for example, transmission via a global communications network or the internet, e.g., via website postings such as by subscription or select or secure access thereto and/or via email and/or via telephone, IR, radio or television other frequency signal, and/or via electronic signals over cable and/or satellite transmission and/or via transmission of disks, cds, computers, hard drives, or other apparatus containing the information in electronic form, and/or transmission of written forms of the information, e.g., via facsimile transmission and the like. Thus, the invention comprehends a user performing methods or using algorithms according to the invention and transmitting information therefrom; for instance, to one or more parties who then further utilize some or all of the data or information, e.g., in the manufacture of products, etc. The invention also comprehends disks, cds, computers, or other apparatus or means for storing or receiving or transmitting data or information containing information from methods and/or use of algorithms of the invention.

Thus, the invention comprehends a method for transmitting information comprising performing a method as discussed herein and transmitting a result thereof.

Further still, the invention comprehends methods of doing business comprising performing some or all of a herein method or use of a herein algorithm, and communicating or transmitting or divulging a result or the results thereof, advantageously in exchange for compensation, e.g., a fee. Advantageously the communicating, transmitting or divulging is via electronic means, e.g., via internet or email, or by any other transmission means herein discussed.

Thus, a first party, "client" can request information, e.g., via any of the herein mentioned transmission means—either previously prepared information or information specially ordered as to a particular tissue or organ—such as, for example, for or on customizing tissue or organ according to one or more parameter requirements, of a second party, "vendor", e.g., requesting information via electronic means such as via internet (for instance request typed into website) or via email, and the vendor can transmit that information, e.g., via any of the transmission means herein mentioned, advantageously via electronic means, such as internet (for instance secure or subscription or select access website) or email: the information can come from performing some or all of a herein method or use of a herein algorithm in response to the request, or from performing some or all of a herein method or use of a herein algorithm, and generating a library of information from performing some or all of a herein method or use of a herein algorithm and meeting the request can then be allowing the client access to the library or selecting data from the library that is responsive to the request.

Accordingly, the invention even further comprehends collections of information, e.g., in electronic form (such as forms of transmission discussed above), from performing a herein method using a herein or portion thereof or using a herein algorithm or performing some or all of a herein method or use of a herein algorithm.

And the invention comprehends linked or networked computers sharing and/or transmitting information from performing a herein method using a herein or portion thereof or using a herein algorithm or performing some or all of a herein method or use of a herein algorithm, such as a server or host computer containing such information and computer or computers, either on the same premises as the server or host computer or remotely situated accessing that information, whereby "transmission" can include the linking of such computers and the access to the information by the remote computer.

Micromachining and Chemical Processing of Silicon and Other Mold Materials

Molds can be made by creating small mechanical structures in silicon, metal, polymer, and other materials using microfabrication processes. These microfabrication processes are based on well-established methods used to make integrated circuits and other microelectronic devices, augmented by additional methods developed by workers in the field of micromachining.

Microfabrication processes that can be used in making the molds disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, *Introduction to Microelectronic Fabrication* (Addison-Wesley Publishing Co., Reading, Mass. 1988); Runyan, et al., *Semiconductor Integrated Circuit Processing Technology* (Addison-Wesley Publishing Co., Reading, Mass. 1990); *Proceedings of the IEEE Micro Electro Mechanical Systems Conference* 1987-1998; Rai-Choudhury, ed., *Handbook of Microlithography, Micromachining & Microfabrication* (SPIE Optical Engineering Press, Bellingham, Wash. 1997). The selection of the material that is used as the mold determines how the surface is configured to form the branching structure. The following methods are preferred for making molds.

Typically, micromachining is performed on standard bulk single crystal silicon wafers of a diameter ranging between about 50 and 300 millimeters (mm), preferably approximately 100 mm, and of thickness ranging between about 200 and 1200 µm. These wafers can be obtained from a large number of vendors of standard semiconductor material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

The geometry of the mold, in particular the number of different feature depths required, is the major factor determining the specific process sequence. The simplest case is that of a single depth dimension for the mold. Specifically, for a silicon substrate, the process sequence is as follows: firsts the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semi-transparent mask. This step can be accomplished using any one of several masking techniques, depending on the desired image resolution. The resist is then developed in an appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

Increased flexibility in the geometry of wafer mold can be obtained by inserting additional cycles of masking and etching, as shown in FIG. 22. Here, a second step in which a masking layer has been applied, and open areas etched, is shown. This modification provides the opportunity to machine channels of varying depths into the wafer mold. To design a mold that is suitable for the culturing of endothelial cells, increased flexibility is very important due to the need for vascular branches with different diameters. The techniques can be extended to provide as many additional layers and different depths as are desired. In addition, these techniques can be used to create secondary patterns within the pattern of microchannels. For example, it may be advantageous to have wells within the microchannels for culturing additional cell types such as feeder cells. The pattern of microchannels also can be designed to control cell growth, for example, to selectively control the differentiation of cells.

Glass and polymeric wafer molds can be fabricated using a similar sequence, but the actual process can be modified by the addition of an intervening masking layer, since etchants for these materials may attack photoresist as well. Such intervening materials simply function to transfer the pattern from the photoresist to interlayer and then on to the wafer below. For silicon etched in one of several wet chemistries, an intervening layer may also be necessary.

The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference*, pp. 1-6 (1996). Porous polymer molds can be formed, for example, by micromolding a polymer containing a volatilizable or leachable material, such as a volatile salt, dispersed in the polymer, and then volatilizing or leaching the dispersed material, leaving a porous polymer matrix in the shape of the mold. Hollow molds can be fabricated, for example, using combinations of dry etching processes (Laermer, et al., "Bosch Deep Silicon Etching: Improving Uniformity and Etch Rate for Advanced MEMS Applications," *Micro Electro Mechanical Systems*, Orlando, Fla., USA, (Jan. 17-21, 1999); Despont, et al., "High-Aspect-Ratio, Ultrathick, Negative-Tone Near-LW Photoresist for MEMS", *Proc. of IEEE 10th Annual International Workshop on MEMS*, Nagoya, Japan, pp. 518-522 (Jan. 26-30, 1997)); micromold creation in lithographically-defined polymers and selective sidewall electroplating; or direct micromolding techniques using epoxy mold transfers.

Polymeric molds can also be made using microfabrication. For example, the epoxy molds can be made as described above, and injection molding techniques can be applied to form the structures. These micromicromolding techniques are relatively less expensive to replicate than the other methods described herein.

Three dimensional printing (3DP) is described by Sachs, et al., *Manufacturing Review* 5, 117-126 (1992) and U.S. Pat. No. 5,204,055 to Sachs, et al. 3DP is used to create a solid object by ink-jet printing a binder into selected areas of sequentially deposited layers of powder. Each layer is created by spreading a thin layer of powder over the surface of a powder bed. The powder bed is supported by a piston, which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

SFF methods other than 3DP that can be utilized to some degree as described herein are stereo-lithography (SLA), selective laser sintering (SLS), ballistic particle manufacturing (BPM), and fusion deposition modeling (FDM). SLA is based on the use of a focused ultra-violet (UV) laser that is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired apparatus is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials. SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

BPM uses an ink-jet printing apparatus wherein an ink-jet stream of liquid polymer or polymer composite material is used to create three-dimensional objects under computer control, similar to the way an ink-jet printer produces two-dimensional graphic printing. The mold is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y. FDM employs an x-y plotter with a z motion to position an extrudable filament formed of a polymeric material, rendered fluid by heat or the presence of a solvent. A suitable system is available from Stratasys, Incorporated of Minneapolis, Minn.

The design of the channels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

Semi-permeable Membrane

A semi-permeable membrane can be used to separate the first mold or polymer scaffold from the second mold or polymer scaffold in the microfabricated apparatuses of the invention. Preferably, the pore size of the membrane is smaller than the cell diameters, thus, cells will not be able to pass through (i.e. a low permeability for animal cells), while low molecular weight nutrients and fluids can pass through (i.e. a high permeability for nutrients), thereby providing adequate cell-to-cell signaling. Cell sizes vary but in general, they are in the range of microns. For example, a red blood cell has a diameter of 8 μm. Perferably, the average membrane pore size is on a submicron-scale to ensure effective screening of the cells.

Semi-permeable membranes of the present invention comprise a wide array of different membrane types and morphologies, which can be classified as follows:

(1) Track-etch membranes consisting of cylindrical through-holes in a dense polymer matrix. These membranes are typically made by ion-etching;

(2) Fibrous membranes made by various deposition techniques of polymeric fibers. While these membranes do not have a well-defined pore topology, production methods have been sufficiently refined so that fibrous membranes have specific molecular weight cut-offs.

Track-etch type membranes are preferred, as they limit the fluid motion in one direction. Preferably, fluid motion is in the vertical direction. Fibrous membranes permit fluid motion both laterally and vertically.

The development of an appropriate membrane will mirror the device progression. Biocompatible and non-degradable membranes can be incorporated in microchannels that are made from poly(dimethyl siloxane) (PDMS). Since PDMS is non-degradable, the membranes do not need to be degradable either. However, degradable membranes and materials for microchannels can also be used. There exists a variety of commercial track-etch membranes with well-defined pore sizes that can be used for this purpose. Care must be taken to properly incorporate the membranes into the existing microchannels without leaking. To this end, the membranes can be bonded with either an oxygen plasma or a silicone-based adhesive. A small recession can be designed into the microchannels so that the membrane can fit tightly therein.

In principle, membrane formation from polymers relies on phase-phase separation. Polymer-solvent interactions are complex, and polymer phase diagrams are significantly more complicated than those for monomeric materials, e.g., metals. Phase separation can be induced either by diffusion (diffusion-induced phase separation or "DIPS") or by thermal means (thermal induced phase separation or "TIPS").

A DIPS system comprises polymer, solvent and non-solvent. The polymer solution is cast as a thin film and then immersed in a coagulation bath containing the non-solvent. This process is governed by the diffusion of various low molecular weight components. The exchange of solvent and non-solvent between the polymer solution and the coagulation bath leads to a change in the composition in the film and phase separation is induced. After some time, the composition of the polymer-rich phase reaches the glass transition composition and the system solidifies. To avoid macrovoid formation, a small amount of non-solvent can be mixed with the polymer solution. In a preferred embodiment, the polymer is polycaprolactone (PCL) and the separation system is chloroform/methanol. Specifically, a polymer solution with a concentration ranging from about 5-10% wt. is made. PCL is prepared by dissolving it in chloroform at room temperature under gentle stirring. Once the polymer has completely dissolved, a small amount is placed on a clean mirror surface, and a membrane knife is used to spread out a film with preset thickness. The thickness of the film can be adjusted by changing the gap between the knife blade and the mirror surface. Once the film has been spread, the entire mirror is immersed in a methanol bath. Phase separation occurs almost instantaneously, but the film and mirror are left in the coagulation bath for up to about 10 minutes to lock in the morphology. A typical membrane thickness is about 100 μm, and the pore size is on the order of about 1 μm, preferably between about 0.01 and 20 μm. Membrane morphology can be varied by altering the composition/concentration of the polymer solution, the film thickness, the components of the coagulation bath, and/or the process conditions. One skilled in the art would understand how to vary any one of these parameters to achieve the desired result.

A TIPS system comprises a thermal gradient to induce phase separation. By choosing a polymer-solvent system that is miscible at high temperatures, but immiscible at low temperatures, e.g., room temperature, phase separation can be induced upon cooling down the polymer solution. In a preferred embodiment, the polymer is PCL and the separation system is DMF/10% $C_3H_8O_3$.

Cells to be Seeded Onto the Mold or Polymer Scaffold

The tissue will typically include one or more types of functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes, kidney cells, pancreatic islet cells, cells present in the intestine, and other parenchymal cells, osteoblasts and other cells forming bone or cartilage, and hematopoietic cells. In some cases it may also be desirable to include nerve cells. The vasculature will typically be formed from endothelial cells. "Parenchymal cells" include the functional elements of an organ, as distinguished from the framework or stroma. "Mesenchymal cells" include connective and supporting tissues, smooth muscle, vascular endothelium and blood cells.

Cells can be obtained by biopsy or harvest from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used.

Methods and drugs for immunosuppression are known to those skilled in the art of transplantation.

Undifferentiated or partially differentiated precursor cells, such as embryonic germ cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stem cells (Furcht, et al., WO 01/11011) can be used in this invention. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. *Nat. Biotechnol.,* 19, 971 (2001)). Undifferentiated or partially differentiated precursor cells can be induced down a particular developmental pathway by culture in medium containing growth factors or other cell-type specific induction factors or agents known in the art. Some examples of such factors are shown in Table 1.

TABLE 1

Selected Examples of Differentiation Inducing Agents

| Agent | Progenitor | Differentiated Cell |
|---|---|---|
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymphocyte[5] |
| β-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth Factor β | Cardiac Fibroblast | Cardiac Myocyte[9] |
| Nerve Growth Factor | Chromaffin Cell | Sympathetic Neuron[10] |
| Steel Factor | Neural Crest | Melanocyte[11] |
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1] Keller, et al. (1999) Exp. Hematol. 27:777-787.
[2] Marti, et al. (1995) Nature. 375:322-325.
[3] Prelle, et al. (2000) Biochem. Biophy. Res. Commun. 277:631-638.
[4] Amedee, et al. (1994) Differentiation. 58:157-164.
[5] Hardt, et al. (1985) Eur. J. Immunol. 15:472-478.
[6] Huelsken, et al. (2001) Cell. 105:533-545.
[7] Ji, et al. (2000) J. Bone Miner. Metab. 18:132-139.
[8] Migliorati, et al. (1987) J. Immunol. 138:3618-3625.
[9] Eghbali, et al. (1991) Proc. Natl. Acad. Sci. USA. 88:795-799.
[10] Niijima, et al. (1995) J. Neurosci. 15:1180-1194.
[11] Guo, et al. (1997) Dev. Biol. 184:61-69.
[12] Ling, et al. (1998) Exp. Neurol. 149:411-423.
[13] Lopez-Fernandez, et al. (2000) J. Biol. Chem. 275:21653-60.
[14] Wang, et al. (1989) Leuk Res. 13:1091-1097.
[15] Lako, et al. (2001) Mech. Dev. 103:49-59.

A stem cell can be any known in the art, including, but not limited to, embryonic stem cells, adult stem cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonal stem cell (ES), as it has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonal germ cells or EG cells). ES and EG cells have been derived from mice, and more recently also from non-human primates and humans. Evans et al. (1981) Nature 292:154-156; Matsui et al. (1991) Nature 353:750-2; Thomson et al. (1995) Proc. Natl. Acad. Sci. USA. 92:7844-8; Thomson et al. (1998) Science 282: 1145-1147; and Shamblott et al. (1998) Proc. Natl. Acad. Sci. USA 95:13726-31.

The terms "stem cells," "embryonic stem cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

The hepatocytes added to the apparatus of the invention can be highly proliferative hepatocytes, known as small hepatocytes (SHCs), which have the ability to proliferate in vitro for long periods of time (Mitaka, et al., *Biochem Biophys Res Commun* 214, 310 (1995); Taneto, et al, *Am J Pathol* 148, 383 (1996)). Small hepatocytes express hepatocyte specific functions such as albumin production (Mitaka, et al., *Hepatology* 29, 111 (1999)).

Methods for Seeding Cells into Molds or Polymer Scaffolds

Cell Seeding

After the mold with the desired high degree of micromachining is prepared, the molds themselves or polymer scaffolds are seeded with the desired cells or sets of cells. The distribution of cells throughout the mold or polymer scaffold can influence both (1) the development of a vascularized network, and (2) the successful integration of the vascular device with the host. The approach used in this invention is to provide a mechanism for the ordered distribution of cells onto the mold or polymer scaffold. Cells that are enriched for extracellular matrix molecules or for peptides that enhance cell adhesion can be used. Cells can be seeded onto the mold or polymer scaffold in an ordered manner using methods known in the art, for example, Teebken, et al., *Eur J. Vasa Endovasc. Surg.* 19, 381 (2000); Ranucci, et al., *Biomaterials* 21, 783 (2000). Also, tissue-engineered devices can be improved by seeding cells throughout the polymeric scaffolds and allowing the cells to proliferate in vitro for a predetermined amount of time before implantation, using the methods of Burg et al., *J. Biomed. Mater. Res* 51, 642 (2000).

For purposes of this invention, "animal cells" can comprise endothelial cells, parenchymal cells, bone marrow cells, hematopoietic cells, muscle cells, osteoblasts, stem cells, mesenchymal cells, stem cells, embryonic stem cells, or fibroblasts. Parenchymal cells can be derived from any organ, including heart, liver, pancreas, intestine, brain, kidney, reproductive tissue, lung, muscle, bone marrow or stem cells.

In one embodiment, the mold or polymer scaffold is first seeded with a layer of parenchymal cells, such as hepatocytes or proximal tubule cells. This layer can be maintained in culture for a week or so in order to obtain a population doubling. It can be maintained in a perfusion bioreactor to ensure adequate oxygen supply to the cells in the interior. The apparatus is then seeded with a layer of endothelial cells and cultured further. In regions where the matrix is resorbed rapidly, the tissue can expand and become permeated with capillaries.

Cell Seeding of Horizontal Layer By Laminar Flow.

A structure comprising joined or fastened molds and/or polymer scaffolds, with or without a semi-permeable membrane between them, is called an "apparatus" for purposes of this invention. Sets of cells can be added to or seeded into the three-dimensional apparatuses, which can serve as a template for cell adhesion and growth by the added or seeded cells. The added or seeded cells can be parenchymal cells, such as hepatocytes or proximal tubule cells. Stem cells can also be used. A second set of cells, such as endothelial cells, can be added to or seeded onto the assembled apparatus through other vessels than those used to seed the first set of cells. The cell seeding is performed by slow flow. As a practical matter, the geometry of the apparatus will determine the flow rates. In general, endothelial cells can enter and form vessel walls in micromachined channels that are about 10-50 µm. Thus, in addition to serving as a mechanical framework for the organ, the assembled apparatus provides a template for all of the microstructural complexity of the organ, so that cells have a mechanical map to locate themselves and form subsystems, such as blood vessels in the liver.

Optionally, functional cells are seeded into both a first and second mold and/or polymer scaffold with microchannels on their surfaces, and the two molds and/or polymer scaffolds are joined or fastened with a semi-permeable membrane between them, allowing gas exchange, diffusion of nutrients, and waste removal. One layer comprises the circulation through which blood, plasma or media with appropriate levels of oxygen can be continuously circulated to nourish the second layer. The second layer comprises a reservoir for the functional cells of an organ, and optionally includes inlets for neural inervation, urine flow, biliary excretion or other activity. This results in an apparatus for making tissue lamina, wherein each of the first and second molds and/or polymer scaffolds and the semi-permeable membrane are comprised of material that is suitable for attachment and culturing of animal cells. The sheet of tissue created by the apparatuses and/or methods of the invention is referred to as "tissue lamina".

Channels in the horizontal direction typically proceed from larger to smaller to larger. The geometries can be as complex as desired in-plane (horizontal direction). Thus, one can use small geometries in-plane (such as horizontal conduits of about 5-20 µm). The alignment of through-holes creates vertical conduits or channels in the z-axis. However, the vertical channels need not go from larger to smaller to larger. In the vertical direction, the vertical channels are typically parallel to each other and have diameters on the micron level, large enough only to allow cell seeding (e.g., hepatocytes are about 40 µm). In one embodiment, different types of cells are seeded horizontally onto different layers of the assembled apparatus. In another embodiment, the different types of cells are seeded using pores or channels from different directions.

Although described herein with particular reference to formation of vascularized tissue, it should be understood that the channels can be used to form lumens for passage of a variety of different fluids, not just blood, but also bile, lymph, nerves, urine, and other body fluids, and for the guided regeneration or growth of other types of cells, especially nerve cells. The tissue layer can include some lumens for forming vasculature and some for other purposes, or be for one purpose, typically providing a blood supply to carry oxygen and nutrients to and from the cells in the tissue.

Molecules such as growth factors or hormones can be covalently attached to the surface of the molds and/or polymer scaffolds and/or semi-permeable membrane to effect growth, division, differentiation or maturation of cells cultured thereon.

Construction of Tissue or Organ Equivalents

Engineered tissue lamina can be systematically folded and compacted into a three-dimensional vascularized structure. The two-dimensional surface of the mold can be varied to aid in the folding and compacting process. For example, the surface can be changed from planar to folded accordion-like. It can be stacked into multiple converging plates. It could be curvilinear or have multiple projections.

Different types of tissue, or multiple layers of the same type of tissue, can be superposed prior to folding and compacting, to create more complex or larger structures. For example, a tubular system can be layered onto a vascular system to fabricate glomerular tissue and collecting tubules for kidneys. Bile duct tubes can be overlaid on vascularized liver or hepatocyte tissue, to generate a bile-duct drainage system. Alveolar or airway tissue can be placed on lung capillaries to make new lung tissue. Nerves or lymphatics can be added using variations of these same general techniques.

Figure 3:
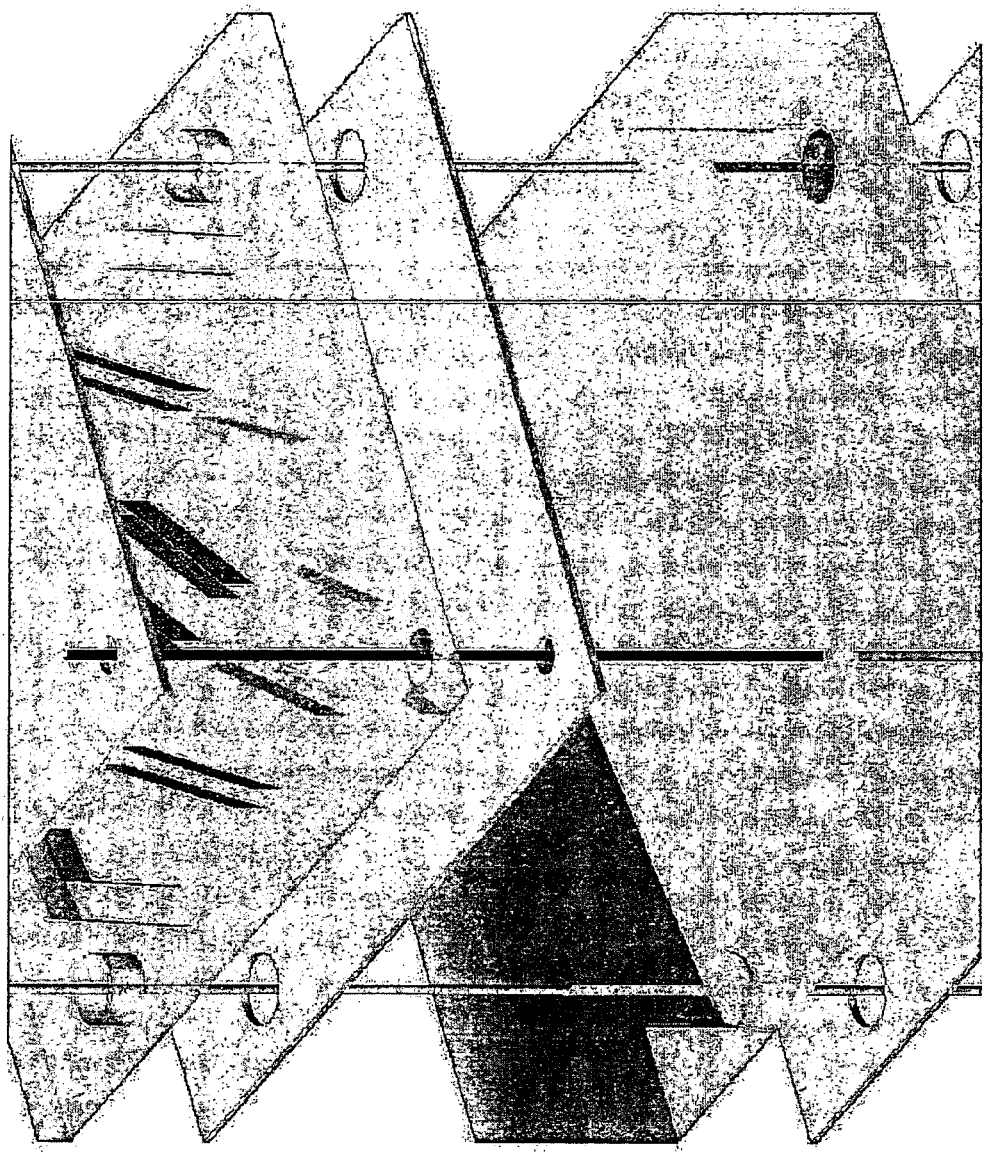
FIG. 3 shows schematic diagram of a cross section of an apparatus for tissue engineering and artificial organ support. The apparatus in FIG. 3A comprises a compartment for circulatory flow, a semi-permeable membrane for mass transfer of oxygen, nutrients and waste, and a compartment for functional cells and excretory system. The apparatus can be seeded with vascular cells or cells that form lumen (e.g. biliary ducts) and functional cells (e.g. hepatocytes).

In addition to embodiments in which a single tissue layer is formed, the apparatus shown in FIG. 3 can be used for three dimensional tissue and organ formation. The addition of the second mold or polymer scaffold allows the functional unit of the organ to be added, and likewise allows precision for patterning of exocrine outflow. For example, in the liver, the parenchymal cells are hepatocytes and the exocrine system is the biliary system. By the addition of the second compartment containing hepatocyes and biliary cells, the functional tissue of the liver can be achieved and biliary excretion can be designed and enfolded.

This patterning can be made more complex with the addition of further layers separated by permeable membranes. Several molds and/or polymer scaffolds, with or without semi-permeable membranes between them, can be stacked in rational arrays to produce complex tissue in 3-dimensional space. These layers of molds and/or polymer scaffolds, and optionally, semi-permeable membranes, can be appropriately interdigitated and connected (e.g. via through-holes) to produce vascular connections through the depths of the stack, as well as excretory outflow systems through the depths of the tracts.

Stacking Molds and/or Polymer Scaffolds to Achieve Three Dimensionality.

Extension of the two-dimensional technology into the third dimension can be accomplished by stacking the two-dimensional layers on top of each other. This stacking method begins with many molds and/or polymer scaffolds produced by the techniques described in previous sections. Once these molds and/or polymer scaffolds (nominally of the same size) are created, they are lain down or bonded to other separate molds and/or polymer scaffolds, atop one another. The layers are connected at points within small and/or midsized vessels by vertical links, which serve as through-holes extending through the z-axis of the molds and/or polymer scaffolds. The pattern of microchannels on the surface of each mold or polymer scaffold can differ or be similar to the previous layer, depending upon fluid mechanical considerations. Alignment provided by vertical links generates vessel structures that extend up into the third (vertical) dimension.

By extending this technology as needed, one can move from the presently achievable formation of small (~100 cm$^2$) tissue sheets, each containing one plane of blood vessels, to the formation of perhaps 100 cm$^3$ of material, enough to build an organ. The process is low-cost, scalable, can be customized for the physiology of a particular patient, and is based upon currently available microfabrication technology.

Fastening the Stacked Layers.

An aspect of this invention is the fastening or sealing of the polymeric mold layers. Preferably, the layers are irreversibly bound before implantation into the host. Depending on the composition of the layered material, the layers can be sealed by solvent bonding; reflow by heating (40° C.); treating surface with oxygen plasma; or by polymer flow at the surface. Biocompatible polymer materials maybe bonded together by plasma activation to form sealed structures (Jo et al., *SPIE* 3877, 222 (1999)). The basic process results in bonded layers with channel architecture closely Silicon-Glass Microfluidic Chambers to Test Sealing of Stacks.

Microfluidic tests have been performed that demonstrate that bonded apparatuses are leakproof and support fluid pressures necessary for dynamic cell seeding. One of the most common methods used to seal micromachined wafers together is anodic bonding, a technique based on the high concentration of mobile ions in many glasses (Camporese, et al., *IEEE Electron. Device Lett. EDL* 2, 61(1981)). This process produces a permanent seal; fracture testing of silicon-glass anodically bonded interfaces produces a failure within the bulk of the glass.

Etched wafers maybe bonded together, producing closed lumens suitable for fluidic experiments. A fluidic test was performed with a mixed-phase flow of alcohol with 10 μm fluorescent microspheres. An unetched glass capping layer was mechanically drilled for inlet and outlet fluid ports, and then anodically bonded to a silicon wafer plasma-etched with the TEP-1-geometry. A permanent seal with no leaks was produced, enabling one to obtain highly accurate pressure and flow data.

Alternatively, the multilayer device of the invention can be configured such that each of the layers has an alignment indentation on one surface of the layer and an alignment protrusion on the opposing surface of another layer. The alignment indentations shaped to mate with the alignment protrusion, so that the layers are held together.

Alternative Methods of Stacking.

To build up the mold and/or polymer scaffold layers by mechanical assembly, the layers can be mechanically mated using biodegradable or non-biodegradable barbs, pins, screws, clamps, staples, wires, string, or sutures (See U.S. Pat. No. 6,143,293). With this mechanical assembly approach, each prefabricated section can comprise different mold and/or polymer scaffold material and/or different mold microstructures. Different sections of these can be seeded with cells before assembly. Cells thus be can be embedded into the mold or polymer scaffold by assembling sections around these components. In addition, surface features on each mold, which are readily fabricated, become part of the internal microstructure (e.g., molded surface channels become conduits for cell infusion, or for blood flow to stimulate angiogenesis). A surface feature on an individual mold or polymer scaffold will become an internal feature when another segment is assembled over it. For example, surface features such as channels can be micromachined into a first mold or polymer scaffold layer. When a second mold or polymer scaffold layer is placed atop that a first layer, the micromachined surface feature becomes an internal feature of the apparatus.

Rolling or Folding to Achieve Three Dimensionality

An alternate method for achieving three-dimensionality is to generate a long strip of polymer mold material, which contains repeating units of the blood vessel network along with through-holes, and to fold the mold film in a z-fold fashion while aligning the through-holes to one another.

The rolling or folding process begins with the generation of a lengthy strip of polymer mold material, which contains a serial array of unit cells each of which is comprised of an array of channels mimicking the vascular network, produced from a wafer mold by molding, embossing, or the like. These unit cells can be identical or can be different. The units are linked to through-holes that provide the vertical channel connections between horizontal blood vessel layers. Once the polymeric scaffold strip has been formed, it is folded in a z-fold fashion, and bonded together so that each fold is attached to the film portions above and below it with alignment to the through-holes.

This roll can be of a length to provide sufficient scaffolding material for an entire human organ, which can be hundreds or even more multiples of the area of a single wafer. Each section of the roll is a sheet of polymeric mold with closed lumens, or vessels. The vessels in each folded section of sheet are connected to a through-hole at the edge of the sheet (for example, one on each side, for inlet and outlet blood flow). During folding, the sheet sections are folded such that the through-hole openings align, forming a vessel in the third (z) dimension. The roll can be in the shape of a spiral, helix, jelly roll or other cylindrically shaped objects.

The described three-dimensional tissue structures can then be implanted into animals or patients by directly connecting the blood vessels to flow into and out of the apparatus. Immediate perfusion of oxygenated blood occurs, which allows survival and function of the entire living mass.

In a one embodiment, tissue-engineered liver is formed. Preferably, tissue engineered liver comprises both functioning hepatocytes and bile ducts. The biliary system of native liver begins with a minute hexagonal bile canaliculus, which is formed from specialization of the adjacent surfaces of individual hepatocytes, which are sealed with tight junctions. These canaliculi are confluent with terminal biliary ductules, which are initially made of squamous cells, but give way to low cubiodal biliary epithelium as they approach the interlobular bile ducts. One liter of bile per day is secreted by hepatocytes and moved out of the liver through this system. There have been previous reports of the formation of duct-like structures in a variety of long-term in vitro and in vivo hepatocyte cultures (Block, et al., *J Cell Biol,* 132, 1133 (1996); Landry, et al., *J Cell Biol,* 101, 914 (1985); Mitaka, et al., *Hepatolog* 29, 111 (1999); Nishikawa, et al., *Exp Cell Res,* 223, 357 (1996); Uyama, et al., *Transplantation* 55, 932 (1993)).

In a yet another embodiment, tissue-engineered kidney is formed. Preferably, tissue engineered kidney comprises functioning proximal tubules. Tissue-engineered kidney functions as a native kidney; glomerular ultrafiltrate can flow from the glomerular endothelium and passes through a semipermeable membrane into a proximal tubule network where reabsorption occurs.

Extracorporeal Support Devices

The invention can be adapted to comprise devices for uses in addition to the formation of implantable tissue. Such devices can be extracorporeal, and may provide partial support function, may extend the time between hospital treatments for patients on chronic organ support therapies, and will improve the quality of life between hospital treatments. For example, the designs can be adapted to produce an extracorporeal renal dialysis device, an extracorporeal liver device, or an extracorporeal artificial lung device. A device/apparatus of the present invention may or may not be supported with living cells loaded or seeded into the device.

The systems of the invention can be implanted into a subject to supplement or replace the biological function of a tissue or organ. Alternatively, the systems can remain ex vivo, serving as extracorporeal devices to supplement or replace biological function. As used herein, the term "biological function" refers to the structural mechanical or metabolic activity of a tissue or organ. Extracorporeal devices of the present invention can comprise hybrid devices suitable for both ex vivo and in vivo use.

EXAMPLES

The Example presented herein demonstrates that present invention can be adapted to suit the needs of all living tissues. The following Example is provided to further describe the invention, and should not be considered to limit its scope in any way.

Example 1

Figure 25:
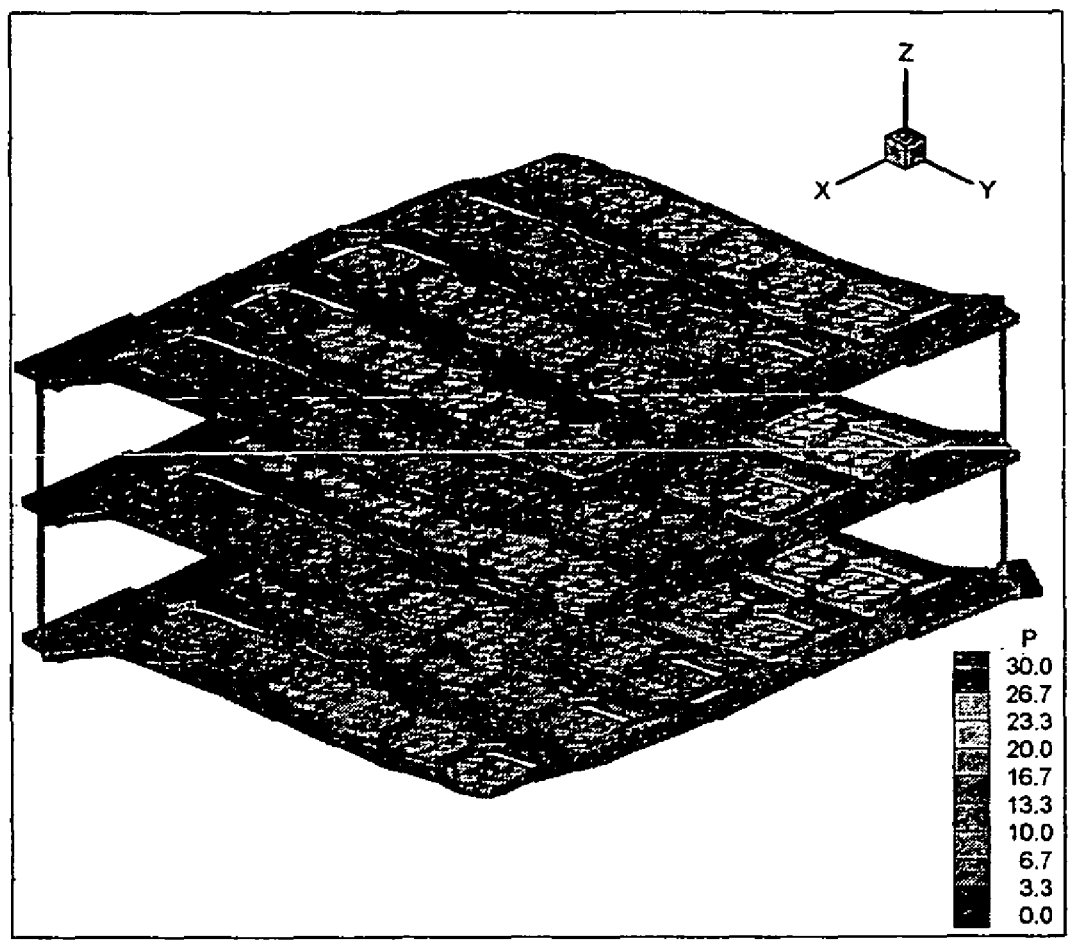
FIG. 25 shows a design known in the art that consists of two-dimensional layers interfaced only at their corners. A similar design is shown in FIG. 4, where the lowest level of flow indicates the smallest vessels.
Figure 26:
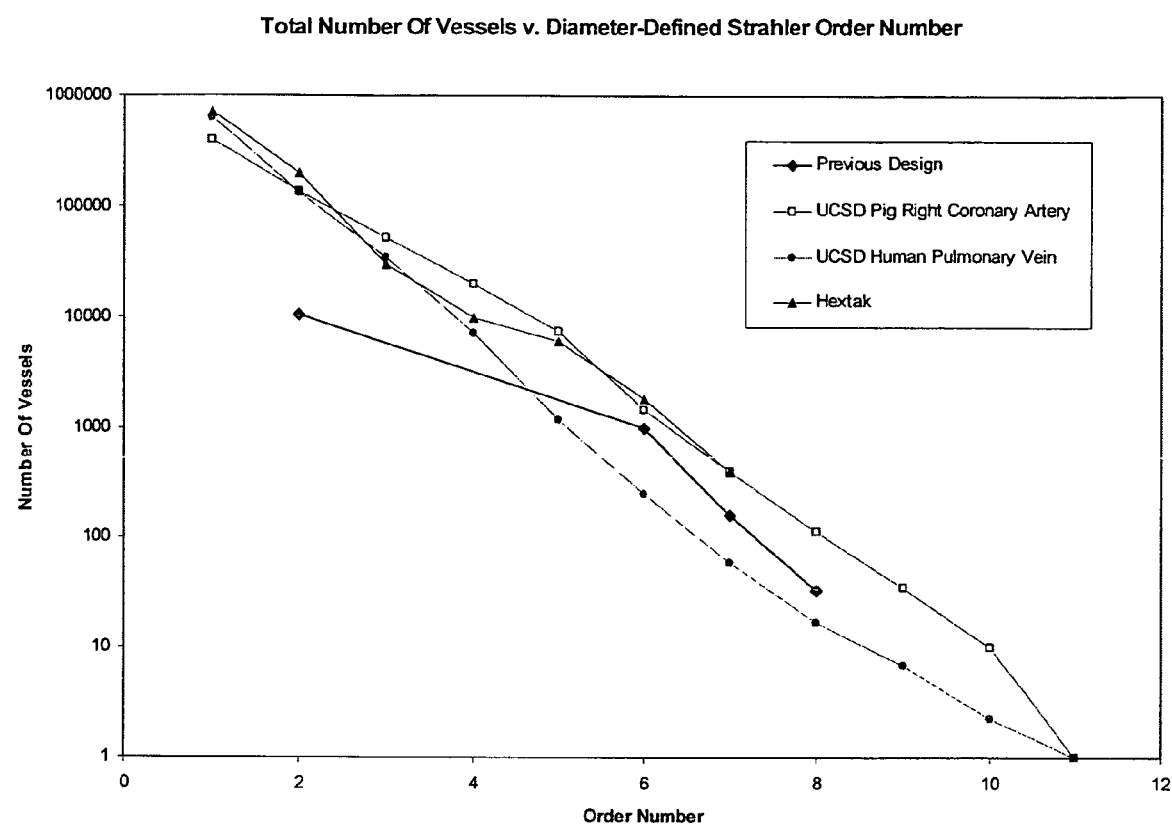
FIG. 26 depicts 1) the design of FIG. 25 (scaled up to organ-size) compared to an organ-sized Hextak and 2) data from two physiological systems (Kassab et al, Am J Physiol 265 (1): H350 (1993); Kassab, Ann Biomed Eng 28 (8): 903 (2000)). Low order numbers represent small vessels.

The most basic characteristic to evaluate in determining whether a fluidic network is desirable for the design of vasculature in a tissue engineered construct is the number of small vessels provided by the network (e.g., diameter less than about 20 microns). Most mass transfer from the blood to the tissue occurs through small vessels, and a large portion of the network's overall resistance lies in the small vessels. Thus, a network with too few small vessels will generally not provide adequate mass transfer to sustain the tissue, and will have too high a resistance to exist in the cardiovascular system. One advantage of the design method provided by the present invention is that networks can have vessel populations matching those of physiological systems, allowing the design of a true vasculature system. Using the diameter-defined Strahler ordering system (Jiang et al., Journal Of Applied Physiology 76 (2):882 (1994)), the number of vessels in a Hextak can be compared to physiological systems and previous scaffold designs. FIG. 25 shows a previous design, which consists of two-dimensional layers interfaced only at their corners. FIG. 26 depicts a comparison of 1) this previous design (scaled up to organ-size) to an organ-sized Hextak and 2) data from two physiological systems (Kassab et al, Am J Physiol 265 (1): H350 (1993); Kassab, Ann Biomed Eng 28 (8): 903 (2000), the contents of which are incorporated herein by reference)). Low order numbers represent small vessels. FIG. 26 shows how the Hextak can have small-vessel populations matching physiological systems, while previous designs have an order of magnitude fewer small vessels.

Since Hextak matches the small-vessel density of physiological tissues more closely, the average distance between a cell in the engineered tissue and a capillary is smaller. In the case of liver, for instance, the maximum distance between hepatocytes and their closest neighboring capillary can be reduced by using a Hextak design. This can enable Hextak designed tissues to nourish the entire tissue with sufficient oxygen, while prior designs would lead to tissue necrosis in some locations where neighboring capillaries are too distant from the hepatocytes. Calculations for liver tissue indicate that the maximum distance between hepatocytes and neighboring capillaries is 100-200 microns, based on oxygen transport considerations. With the Hextak design, this requirement is achievable throughout the organ, while previous two-dimensional layering designs would result in insufficiently oxygenated regions. This oxygen transport advantage of Hextak designs is true for many organs.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

The invention claimed is:

1. A method of modeling and designing a physiologically based fluidic network in a three-dimensional construct for use as an organ simulant for a specific organ, comprising the steps of:

generating an initial design of an initial network in node-vessel format by stacking two-dimensional layers comprised of vessels connected by nodes and interconnecting the layers with vertical vessels such that the initial design is a three-dimensional design of a biological construct;

translating the initial design from node-vessel format into a set of matrix equations relating a pressure and a resistance for each vessel, thereby defining flow behavior in the network;

setting constraints on the set of matrix equations and determining a flow rate in each vessel, wherein the constraints include at least one physiological parameter associated with the specific organ;

solving the set of matrix equations for the pressure and resistance of each vessel based on the flow rate in each vessel and the constraints;

determining a geometry of each vessel on the basis of the corresponding resistance, thereby defining a final design of a final biological construct; and producing the final biological construct for use as an organ simulant.

2. The method according to claim 1, wherein the generating step comprises the steps of: creating layers wherein the vessels are generated using a hexagonal fractal algorithm; stacking the layers to produce a three-dimensional design; connecting nodes which are vertically aligned between stacked layers; and adding inlet and outlet vessels to the initial design.

3. The method according to claim 1, wherein at least two different layer designs are used in generating the initial design.

4. The method according to claim 1, wherein the node-vessel format comprises a list of vessels and a list of nodes defining locations where vessels connect, wherein each vessel connects two nodes.

5. The method according to claim 1, further comprising a step of receiving a branching pattern indicating a number of vessels, interconnections between the vessels, and a tissue size to be supported by the fluidic network; and wherein the initial design is generated on the basis of the received branching pattern.

6. The method according to claim 1, further comprising a step of applying a branching diameter rule to the initial design such that only similarly sized vessels are connected to each other.

7. The method according to claim 1, wherein the geometry of each vessel includes a width and a depth and is determined by calculating the width on the basis of the corresponding resistance and the depth corresponds to an etch depth.

8. The method according to claim 1, wherein the producing step is by soft-lithography techniques for use in tissue-engineered organs.

9. The method according to claim 1, wherein one of the constraints is a distance between the vessels to allow proper supply of nutrients and oxygen as well as processing of waste.

10. The method according to claim 1, wherein the initial network is designed to accommodate blood and setting the constraints includes matching physiological parameters at a boundary of the initial network with a boundary of the specific organ to allow implantation without disturbing blood flow.

11. The method according to claim 1, wherein the determining step includes creating a pattern with the vessels spaced evenly throughout that avoids sharp angles between intersecting vessels in the two-dimensional layers by defining a reference direction in a plane, defining a vessel length L, defining an origin, defining a maximum pattern diameter, creating three vessels with one node at the origin, each vessel having a length L wherein one of the vessels extends parallel to the reference direction, one of the vessels at 120 degrees from the reference direction, and one of the vessels at 240 degree from the reference direction, and iterating through each node by redefining the reference direction as a direction of a vessel connected to that node and redefining the origin as the current node.

12. The method according to claim 11, further comprising wherein the determining step further includes repeating iterating at each node until no nodes are outside the maximum network diameter.

13. The method according to claim 1, wherein the at least one physiological parameter is wall shear stress and the step of solving includes solving the set of matrix equations for flow in addition to pressure and resistance.

14. A method of designing and producing an organ simulant to replace or augment a target organ, comprising the steps of:
generating a three-dimensional design of the organ simulant having a construct that defines a physiologically based fluidic network, wherein the design is in node-vessel format by stacking a plurality of two-dimensional layers comprised of vessels connected by nodes and interconnecting the layers with vertical vessels;
translating the three-dimensional design from node-vessel format into a set of matrix equations relating performance parameters for each vessel;
setting constraints on the set of matrix equations to solve the set of matrix equations to approximately match the performance parameters to physiological parameters of the target organ;
determining a geometry of each vessel on the basis of the solution of the set of matrix equations, thereby defining a physiologically based fluidic network of a revised three-dimensional design of the organ simulant; and
producing the revised three-dimensional design of the organ simulant.

15. The method according to claim 14, further comprising the step of determining a flow rate, pressure and resistance in each vessel.

16. The method according to claim 14, wherein the constraints include a distance between the vessels to allow proper supply of nutrients and oxygen as well as processing of waste.

17. The method according to claim 14, wherein the network is designed to accommodate blood and setting the constraints includes matching the physiological parameters at a boundary of the physiologically based fluidic network with a boundary of the target organ to allow implantation without disturbing blood flow.

18. The method according to claim 14, wherein the determining step includes creating a pattern with the vessels spaced evenly throughout that avoids sharp angles between intersecting vessels in the two-dimensional layers by defining a reference direction in a plane, defining a vessel length L, defining an origin, defining a maximum pattern diameter, creating three vessels with one node at the origin, each vessel having a length L wherein one of the vessels extends parallel to the reference direction, one of the vessels at 120 degrees from the reference direction, and one of the vessels at 240 degree from the reference direction, and iterating through each node by redefining the reference direction as a direction of a vessel connected to that node and redefining the origin as the current node.

19. The method according to claim 18, wherein the determining step further includes repeating iterating at each node until no nodes are outside the maximum network diameter.

* * * * *